(12) United States Patent
Alonso-Alija et al.

(10) Patent No.: US 7,074,790 B2
(45) Date of Patent: Jul. 11, 2006

(54) 5-ETHYLIMIDAROTRIAZONES

(76) Inventors: Cristina Alonso-Alija, August-Macke-Weg 3, Haan (DE) D-42791; Heike Gielen-Haertwig, Claire-Waldoff-Str.23, Monheim (DE) D-40789; Martin Michels, Nibelungenstr. 65, Solingen (DE) D-42653; Dagmar Karthaus, Mittelstr. 36, Solingen (DE) D042697; Hilmar Bischoff, Am Rohm 78, Wuppertal (DE) D-42113; Nils Burkhardt, Unterste Dillenberg 16, Velbert (DE) D-42553; Volker Geiss, Peddenkamp 58, Ratingen (DE) D40883; Karl-Heinz Schlemmer, Wildsteig 22 a, Wuppertal (DE) D-42113; Nigel Cuthbert, Abbottshood Farm, Greenway, Halberton, Tiverton, Devon (GB) EX16 7AE; Mary F. Fitzgerald, 2 Patermoster Court, Cassington Road, Yarnton, Oxfordshire (GB) OX5 1QB; Graham Sturton, 184 Windsor Road, Maidenhead, Berkshire (GB) SL6 2DW; Ulrich Niewöhner, deceased, late of Wermelskirchen (DE); by Maria Theresia Niewöhner, legal representative, Gartenstr. 3, Wermelskirchen (DE) D42929

( * ) Notice: Subject to any disclaimer, the term of this patent is extended or adjusted under 35 U.S.C. 154(b) by 33 days.

(21) Appl. No.: 10/514,672

(22) PCT Filed: May 5, 2003

(86) PCT No.: PCT/EP03/04665

§ 371 (c)(1),
(2), (4) Date: Jul. 15, 2005

(87) PCT Pub. No.: WO03/097645

PCT Pub. Date: Nov. 27, 2003

(65) Prior Publication Data

US 2006/0040942 A1   Feb. 23, 2006

(30) Foreign Application Priority Data

May 16, 2002   (GB) .................. 0211257.1

(51) Int. Cl.
C07D 487/04   (2006.01)
A61K 31/53    (2006.01)
A61K 31/4188  (2006.01)
A61P 19/02    (2006.01)
A61P 11/00    (2006.01)

(52) U.S. Cl. .................. 514/243; 544/184
(58) Field of Classification Search ........... 544/184; 514/243
See application file for complete search history.

(56) References Cited

U.S. PATENT DOCUMENTS 4,278,673 A   7/1981 Hartley et al.

FOREIGN PATENT DOCUMENTS

WO   9967244   12/1999

OTHER PUBLICATIONS

Lucas et al. Pharmacological Reviews 52 (3), 375-413, 2000.*

* cited by examiner

*Primary Examiner*—Venkataraman Balasubramanian

(57) ABSTRACT

The invention relates to novel 5-ethyl-imidazotriazinones, processes for their preparation and their use in medicaments, esp. for the treatment and/or prophylaxis of inflammatory processes and/or immune diseases.

8 Claims, No Drawings

5-ETHYLIMIDAROTRIAZONES

The invention relates to novel 5-ethyl-imidazotriazinones, processes for their preparation and their use in medicaments, esp. for the treatment and/or prophylaxis of inflammatory processes and/or immune diseases.

Phosphodiesterases (PDEs) are a family of enzymes responsible for the metabolism of the intracellular second messengers cAMP (cyclic adenosine monophosphate) and cGMP (cyclic guanosine monophosphate). PDE 4, as a cAMP specific PDE, catalyses the conversion of cAMP to AMP and is the major if not sole isoform of the phosphodiesterase enzymes present in inflammatory and immune cell types. Inhibition of this enzyme leads to the accumulation of cAMP which, in these cells, leads to the inhibition of a range of pro-inflammatory functions. Uncontrolled production of inflammatory mediators can lead to acute and chronic inflammation, tissue damage, multi-organ failures and to death. Additionally, elevation of phagocyte cAMP leads to inhibition of oxygen radical production. This cell function is more sensitive than others such as aggregation or enzyme release.

It is now recognised that both asthma and COPD (Chronic obstructive pulmonary disease) are chronic inflammatory lung diseases. In the case of asthma the eosinophil is the predominant infiltrating cell. Subsequent release of superoxide radicals as well as damaging cationic proteins from these infiltrating cells are believed to play a role in the progression of the disease and development of airway hyper-reactivity.

By contrast, in COPD the neutrophil is the predominant inflammatory cell type found in the lungs of sufferers. The action of mediators and proteases released in the environment of the lung is believed to result in the irreversible airway obstruction seen in COPD. In particular the action of proteases in degrading the lung matrix results in fewer alveoli and is likely to be the major cause of accelerated long term lung function decline seen in this disease.

Treatment with a PDE 4 inhibitor is expected to reduce the inflammatory cell burden in the lung in both of these diseases [M. S. Barnette, "PDE 4 inhibitors in asthma and chronic obstructive pulmonary disease", in: Progress in Drug Research, Birkhäuser Verlag, Basel, 1999, pp. 193–229; H. J. Dyke and J. G. Montana, "The therapeutic potential of PDE 4 inhibitors", Exp. Opin. Invest. Drugs 8, 1301–1325 (1999)].

WO 99/24433 and WO 99/67244 describe 2-phenyl-imidazotriazinones as synthetic intermediates for the synthesis of 2-(aminosulfonyl-phenyl)-imidazotriazinones as inhibitors of cGMP-metabolizing phosphodiesterases.

U.S. Pat. No. 4,278,673 discloses 2-aryl-imidazotriazinones with cAMP-phosphodiesterase inhibitory activity for the treatment of i.a. asthma.

The present invention relates to compounds of the general formula (I)

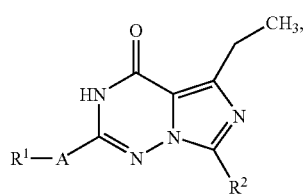

(I)

in which

A denotes phenylene or pyridinylene, which can be substituted by 0 to 3 residues selected independently from the group consisting of halogen, $(C_1-C_4)$-alkyl, trifluoromethyl, cyano, nitro, $(C_1-C_4)$-alkoxy and trifluoromethoxy, $R^1$ denotes hydroxy or a group of the formula $-NR^3R^4$, $-X-C(=O)-OR^5$ or $-X-C(=O)-NR^6R^7$, wherein X denotes a bond, $-CH_2-$, $-CH_2-CH_2-$ or $-CH=CH-$, $R^3$ and $R^4$ are independently selected from the group consisting of hydrogen, $(C_1-C_6)$-alkyl, $(C_3-C_7)$-cycloalkyl, $(C_1-C_6)$-alkanoyl and $(C_6-C_{10})$-aroyl, wherein $(C_1-C_6)$-alkyl can be further substituted with 0 to 3 substituents selected independently from the group consisting of $(C_3-C_7)$-cycloalkyl and $(C_6-C_{10})$-aryl, $R^5$ denotes hydrogen or $(C_1-C_6)$-alkyl, $R^6$ and $R^7$ are independently selected from the group consisting of hydrogen, $(C_1-C_6)$-alkyl, $(C_3-C_7)$-cycloalkyl and $(C_6-C_{10})$-aryl, or together with the nitrogen atom to which they are attached form a 4- to 7-membered heterocyclic ring which may contain one additional ring heteroatom selected from N, O or S, $R^2$ denotes $(C_3-C_{10})$-cycloalkyl, which is optionally substituted up to two times by residues selected independently from the group consisting of $(C_1-C_6)$-alkyl, $(C_1-C_6)$-alkoxy, hydroxy, halogen, trifluoromethyl and oxo.

The compounds according to the invention can also be present in the form of their salts, solvates or solvates of the salts.

Depending on their structure, the compounds according to the invention can exist in stereoisomeric forms (enantiomers, diastereomers). The invention therefore relates to the enantiomers or diastereomers and to their respective mixtures. Such mixtures of enantiomers and/or diastereomers can be separated into stereoisomerically unitary constituents in a known manner.

The invention also relates to tautomers of the compounds, depending on the structure of the compounds.

Salts for the purposes of the invention are preferably physiologically acceptable salts of the compounds according to the invention.

Physiologically acceptable salts of the compounds (I) include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene-disulphonic acid, acetic acid, propionic acid, lactic acid, tartaric acid, malic acid, citric acid, fumaric acid, maleic acid and benzoic acid.

Physiologically acceptable salts of the compounds (I) also include salts of customary bases, such as for example and preferably alkali metal salts (for example sodium and potassium salts, alkaline earth metal salts (for example calcium and magnesium salts) and ammonium salts derived from ammonia or organic amines having 1 to 16 carbon atoms, such as illustratively and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

Solvates for the purposes of the invention are those forms of the compounds that coordinate with solvent molecules to form a complex in the solid or liquid state. Hydrates are a specific form of solvates, where the coordination is with water.

For the purposes of the present invention, the substituents have the following meanings, unless otherwise specified:

Alkyl per se and "alk" and "alkyl" in alkoxy, alkanoyl represent a linear or branched alkyl radical having generally 1 to 6, preferably 1 to 4 and particularly preferably 1 to 3 carbon atoms, representing illustratively and preferably methyl, ethyl, n-propyl, isopropyl, tert-butyl, n-pentyl and n-hexyl.

Alkoxy illustratively and preferably represents methoxy, ethoxy, n-propoxy, isopropoxy, tert-butoxy, n-pentoxy and n-hexoxy.

Alkanoyl illustratively and preferably represents acetyl and propanoyl.

Aroyl illustratively and preferably represents benzoyl.

Cycloalkyl represents a cycloalkyl group having generally 3 to 7 and preferably 5 to 6 carbon atoms, illustratively and preferably representing cyclopropyl, cyclobutyl, cyclopentyl, cyclohexyl and cycloheptyl.

Aryl per se and in arylamino and in arylcarbonyl represents a mono- to tricyclic aromatic carbocyclic radical having generally 6 to 10 carbon atoms, illustratively and preferably representing phenyl.

Halogen represents fluorine, chlorine, bromine and iodine.

A preferred embodiment of the invention relates to compounds of the general formula (I), in which
A denotes 1,3- or 1,4-phenylene, which can be substituted by 0 to 3 residues selected independently from the group consisting of fluoro, chloro, bromo, methyl, trifluoromethyl, methoxy, ethoxy and trifluoromethoxy,
$R^1$ denotes hydroxy or a group of the formula —$NR^3R^4$, —X—C(=O)—$OR^5$ or —X—C(=O)—$NR^6R^7$, wherein
X denotes a bond, —$CH_2$—$CH_2$— or —CH=CH—,
$R^3$ denotes hydrogen,
$R^4$ denotes hydrogen, ($C_1$–$C_4$)-alkyl or ($C_1$–$C_5$)-alkanoyl, wherein ($C_1$–$C_4$)-alkyl can be further substituted with 0 to 3 substituents selected independently from the group consisting of cyclopentyl, cyclohexyl or phenyl,
$R^5$ denotes hydrogen,
$R^6$ and $R^7$ are independently selected from the group consisting of hydrogen, ($C_1$–$C_4$)-alkyl and ($C_5$–$C_6$)-cycloalkyl, or together with the nitrogen atom to which they are attached form a 5- to 6-membered heterocyclic ring which may contain one additional ring heteroatom selected from N, O or S,
$R^2$ denotes ($C_4$–$C_7$)-cycloalkyl, which is optionally substituted up to two times by residues independently selected from the group consisting of ($C_1$–$C_4$)-alkyl, ($C_1$–$C_4$)-alkoxy, hydroxy, fluoro, trifluoromethyl and oxo.

Another preferred embodiment of the invention relates to compounds of the general formula (I), in which
A denotes 1,3- or 1,4-phenylene,
$R^1$ denotes hydroxy or a group of the formula —$NR^3R^4$, —X—C(=O)—$OR^5$ or —X—C(=O)—$NR^6R^7$, wherein
X denotes a bond,
$R^3$ denotes hydrogen,
$R^4$ denotes hydrogen, ($C_1$–$C_4$)-alkyl, ($C_1$–$C_5$)-alkanoyl, cyclohexyl methyl or benzyl,
$R^5$ denotes hydrogen,
$R^6$ denotes hydrogen, methyl or ethyl,
$R^7$ denotes hydrogen, ($C_1$–$C_4$)-alkyl, cyclopentyl or cyclohexyl, or
$R^6$ and $R^7$ together with the nitrogen atom to which they are attached form a morpholino or piperidino ring,
$R^2$ denotes ($C_4$–$C_6$)-cycloalkyl, which is optionally substituted up to two times by identical or different ($C_1$–$C_4$)-alkyl residues.

Another preferred embodiment of the invention relates to compounds of the general formula (I), in which
$R^1$ and A have the meaning indicated in claim 3,
$R^2$ denotes cyclobutyl, cyclopentyl or cis-4-tert-butyl-cyclohexyl.

The invention furthermore provides a process for preparing the compounds of the general formula (I) according to the invention, characterized in that
compounds of the general formula (II)

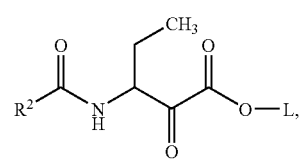

in which
$R^2$ is as defined above
and
L represents straight-chain or branched alkyl having up to 4 carbon atoms,
are condensed with compounds of the general formula (III)

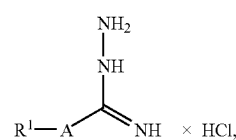

in which
A and $R^1$ are as defined above,
preferably using ethanol as a solvent, to the compounds of the general formula (IV)

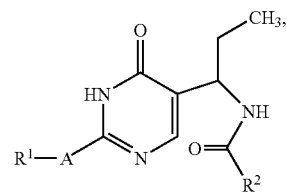

in which
A, $R^1$ and $R^2$ are as defined above,
which can optionally after isolation be reacted with a dehydrating agent, preferably phosphorous oxytrichloride, to yield the compounds of the general formula (I).

The compounds of the general formula (IV) can alternatively be prepared by

[A] condensation of compounds of the general formula (IIa)

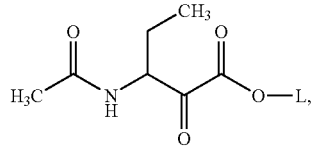

in which
L is as defined above,
with compounds of the general formula (III) to compounds of the general formula (IVa)

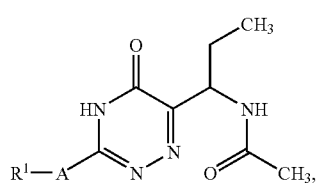

in which
A and $R^1$ are as defined above,
preferably using ethanol as a solvent,

[B] followed by hydrolysis of the compounds of the general formula (IVa) to compounds of the general formula (V)

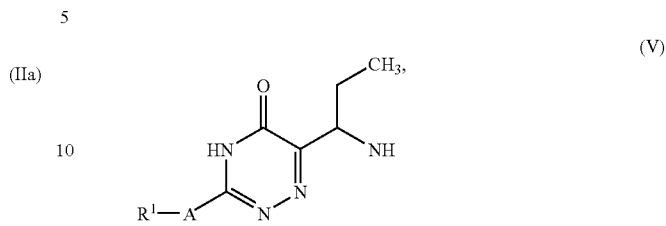

in which
A and $R^1$ are as defined above,

[C] and finally by condensation of the compounds of the general formula (V) with compounds of the general formula (VI)

in which
$R^2$ is as defined above, and
T represents a leaving group, preferably chlorine.

The process according to the invention can be illustrated using the following scheme as an example:

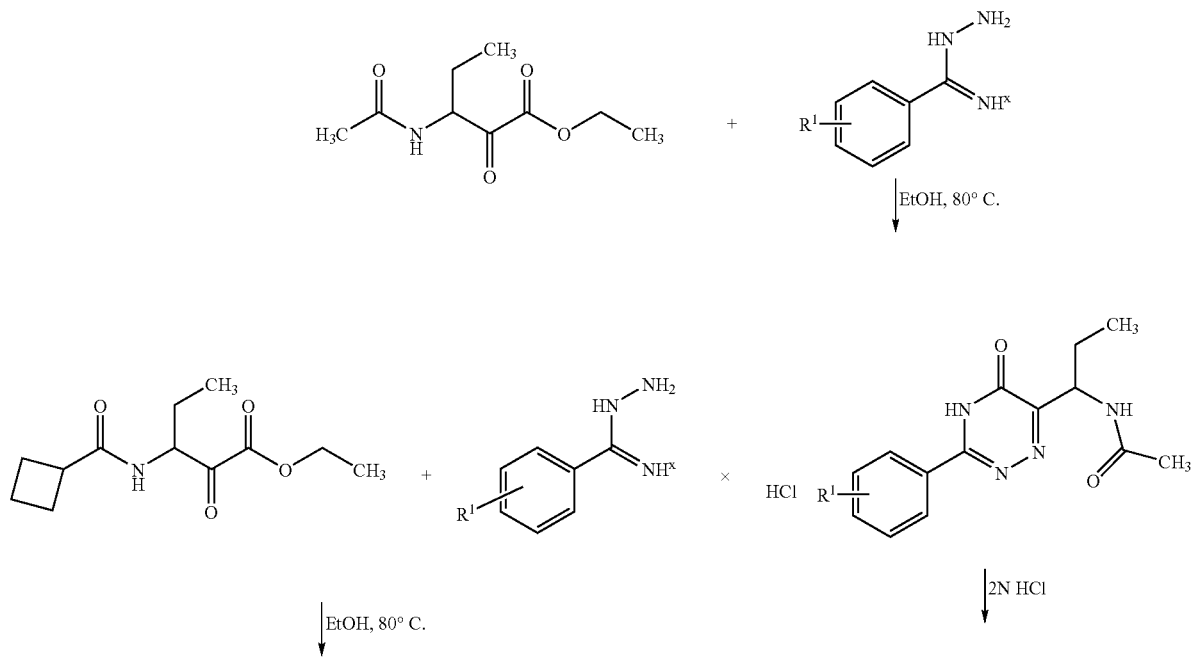

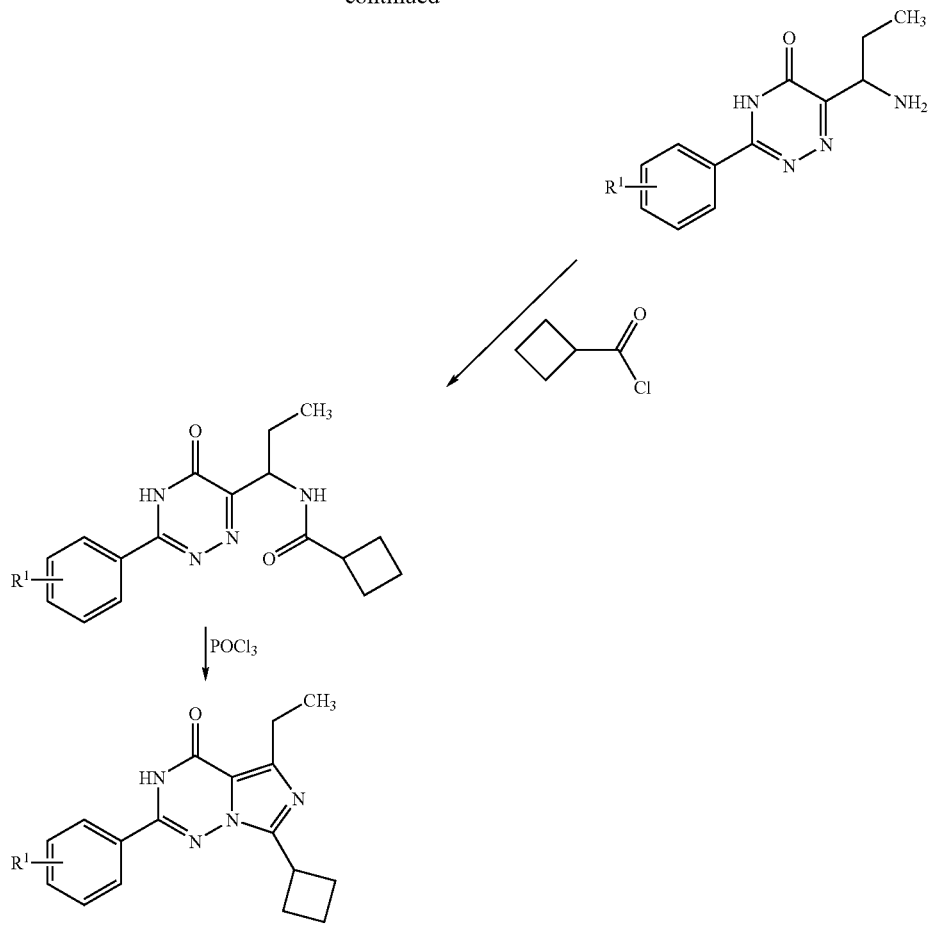

Solvents which are suitable for the individual steps are the customary organic solvents which do not change under the reaction conditions. These preferably include ethers, such as diethyl ether, dioxan, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethane, trichloroethylene or chlorobenzene, or ethyl acetate, dimethylformamide, dimethylsulfoxide, hexamethylphosphoric triamide, acetonitrile, acetone, or pyridine. It is also possible to use mixtures of the above-mentioned solvents. Particular preference is given to ethanol for the reaction (II)/(IIa)+(III)→(IV)/(IVa), and dichloroethane for the cyclisation (IV)→(I).

The reaction temperature can generally be varied within a relatively wide range. In general, the reaction is carried out in a range of from −20° C. to 200° C., preferably of from 0° C. to 100° C.

The process steps according to the invention are generally carried out under atmospheric pressure. However, it is also possible to operate under super atmospheric pressure or under reduced pressure (for example, in a range from 0.5 to 5 bar).

The compounds of the general formula (IVa) are preferably hydrolysed to compounds of the general formula (V) under acidic conditions as for example in refluxing 2N hydrochloric acid.

The compounds of the general formula (V) are condensed with the compounds of the general formula (VI) to compounds of the general formula (IV) in inert solvents, if appropriate in the presence of a base.

Suitable inert solvents are the customary organic solvents which do not change under the reaction conditions. These preferably include ethers, such as diethyl ether, dioxan, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethylformamide, dimethylsulfoxide, hexamethylphosphoric triamide, acetonitrile, acetone, or pyridine. It is also possible to use mixtures of the above-mentioned solvents.

Suitable bases are generally alkali metal hydrides or alkali metal alkoxides, such as, for example, sodium hydride or potassium tert-butoxide, or cyclic amines, such as, for example, piperidine, pyridine, 4-N,N-dimethylaminopyridine or ($C_1$–$C_4$)-alkylamines, such as, for example, triethylamine. Preference is given to triethylamine, pyridine and/or 4-N,N-dimethylaminopyridine.

The base is generally employed in an amount of from 1 mol to 4 mol, preferably from 1.2 mol to 3 mol, in each case based on 1 mol of the compound of the formula (V).

The reaction temperature can generally be varied within a relatively wide range. In general, the reaction is carried out in a range of from −20° C. to 200° C., preferably of from ° C. to 100° C.

Some of the compounds of the general formula (II) are known, or they are novel, and they can then be prepared by converting compounds of the general formula (VI)

$$R^2 \underset{\underset{O}{\|}}{C} T, \quad (VI)$$

in which
R² is as defined above, and
T represents a leaving group, preferably chlorine,
initially by reaction with α-aminobutyric acid in inert solvents, if appropriate in the presence of a base and trimethylsilyl chloride, into the compounds of the general formula (VII)

$$R^2 \underset{\underset{O}{\|}}{C} \underset{H}{N} \underset{CO_2H}{\overset{CH_3}{\underset{|}{CH}}}, \quad (VII)$$

in which
R² is as defined above,
and finally reacting with the compound of the formula (VII)

$$Cl \underset{\underset{O}{\|}}{C} CO_2L, \quad (VIII)$$

in which
L is as defined above,
in inert solvents, if appropriate in the presence of a base.

The compounds of the general formula (IIa) can be prepared analogously.

Suitable solvents for the individual steps of the process are the customary organic solvents which do not change under the reaction conditions. These preferably include ethers, such as diethyl ether, dioxan, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethylformamide, dimethylsulfoxide, hexamethylphosphoric triamide, acetonitrile, acetone, or pyridine. It is also possible to use mixtures of the above-mentioned solvents. Particular preference is given to dichloromethane for the first step and to a mixture of tetrahydrofuran and pyridine for the second step.

Suitable bases are generally alkali metal hydrides or alkali metal alkoxides, such as, for example, sodium hydride or potassium tert-butoxide, or cyclic amines, such as, for example, piperidine, pyridine, 4-N,N-dimethylaminopyridine or ($C_1$–$C_4$)-alkyl-amines, such as, for example, triethylamine. Preference is given to triethylamine, pyridine and/or 4-N,N-dimethylaminopyridine.

The base is generally employed in an amount of from 1 mol to 4 mol, preferably from 1.2 mol to 3 mol, in each case based on 1 mol of the compound of the formula (VII).

The reaction temperature can generally be varied within a relatively wide range. In general, the reaction is carried out in a range of from −20° C. to 200° C., preferably of from 0° C. to 100° C.

The compounds of the general formulae (VI) and (VIII) are known per se, or they can be prepared by customary methods.

The compounds of the general formula (III) are known or can be prepared by
reacting compounds of the general formula (IX)

$$R^1-A-Y, \quad (IX)$$

in which
A and R¹ are as defined above, and
Y represents a cyano, carboxyl, methoxycarbonyl or ethoxycarbonyl group, with ammonium chloride in toluene and in the presence of trimethylaluminium in hexane in a temperature range from −20° C. to room temperature, preferably at 0° C. and atmospheric pressure, and reacting the resulting amidine, if appropriate in situ, with hydrazine hydrate.

The compounds of the general formula (IX) are known per se, or they can be prepared by customary methods.

[A] Alternatively, compounds of the general formula (I), wherein A is phenyl and R¹ is amino, can be prepared by reduction of compounds (X)

(X)

wherein
R² has the meaning indicated above, and $R^{1-1}$ represents nitro, preferably with palladium on charcoal and hydrogen.

Suitable inert solvents for the reduction are the customary organic solvents which do not change under the reaction conditions. These preferably include ethers, such as diethyl ether, dioxan, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethylformamide, dimethylsulfoxide, hexamethylphosphoric triamide, acetonitrile, acetone, or pyridine. It is also possible to use mixtures of the above-mentioned solvents. Preferred is tetrahydrofuran.

The free amines yielded by this reduction can successively be converted to other amino derivatives, e.g by reductive amination with carbonyl derivatives in the presence of cyanoborohydride (yielding secondary amines), or by reaction with acylating agents such as acid chlorides (yielding amides).

[B] Alternatively, compounds of the general formula (I), wherein A is phenyl and $R^1$ is aminocarbonyl or carboxyl, can be prepared by saponification of compounds (X), wherein $R^2$ has the meaning indicated above, and $R^{1-1}$ represents cyano, preferably with potassium carbonate and hydrogen peroxide.

Suitable inert solvents for the reduction are the customary organic solvents which do not change under the reaction conditions. These preferably include ethers, such as diethyl ether, dioxan, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethylformamide, dimethylsulfoxide, hexamethylphosphoric triamide, acetonitrile, acetone, or pyridine. It is also possible to use mixtures of the above-mentioned solvents. Preferred is ethanol/water.

The amides or carboxylic acids yielded by this saponification can successively be converted to other carbonyl derivatives by standard procedures, e.g. amide coupling or esterification.

[C] Alternatively, compounds of the general formula (I), wherein A is phenyl and $R^1$ is —X—C(=O)—$OR^5$ or —X—C(=O)—$NR^6R^7$, wherein X denotes —CH=CH— and $R^5$, $R^6$ and $R^7$ are as described above, can be prepared by coupling of compounds (X), wherein $R^2$ has the meaning indicated above, and $R^{1-1}$ represents-bromo, with the respective acrylic acid derivatives.

This coupling preferably takes place in the presence of dichlorobis(triphenyl-phosphine)palladium(II) and a base, e.g. triethylamine. The acrylic acid derivatives yielded by this coupling can successively be converted to other derivatives, e.g. by hydrogenation of the double bond.

Compounds of the general formula (X) can be prepared by reaction of compounds of the general formula (Va)

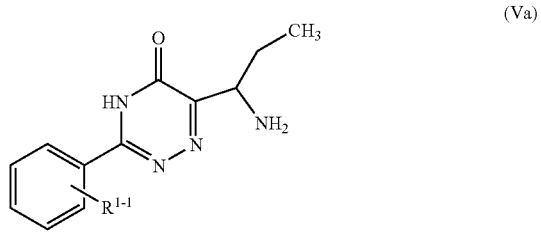

(Va)

with compounds of the general formula (VI) in the presence of phosphoroxychloride.

Suitable inert solvents for the reaction with carbonyl compounds are the customary organic solvents which do not change under the reaction conditions. These preferably include ethers, such as diethyl ether, dioxan, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene. It is also possible to use mixtures of the above-mentioned solvents. Preferred is dichloroethane.

Compounds of the general formula (Va) are compounds of the general formula (V), wherein A represents phenyl and $R^1$ represents a nitro, cyano or bromo group. They can be prepared analogously to compounds of the general formula (V).

The compounds of the general formula (I) inhibit the PDE 4 resident in the membranes of human neutrophils. One measured functional consequence of this inhibition was inhibition of superoxide anion production by stimulated human neutrophils.

The compounds of the general formula (I) can therefore be employed in medicaments for the treatment of inflammatory processes, esp. acute and chronic inflammatory processes, and/or immune diseases.

The compounds according to the invention are preferably suitable for the treatment and prevention of inflammatory processes, i.e. acute and chronic inflammatory processes, and/or immune diseases, such as emphysema, alveolitis, shock lung, all kinds of chronic obstructive pulmonary diseases (COPD), adult respiratory distress syndrome (ARDS), asthma, bronchitis, cystic fibrosis, eosinophilic granuloma, arteriosclerosis, arthrosis, inflammation of the gastro-intestinal tract, myocarditis, bone resorption diseases, reperfusion injury, Crohn's disease, ulcerative colitis, systemic lupus erythematosus, type I diabetes mellitus, psoriasis, anaphylactoid purpura nephritis, chronic glomerulonephritis, inflammatory bowel disease, atopic dermatitis, other benign and malignant proliferative skin diseases, allergic rhinitis, allergic conjunctivitis, vernal conjunctivitis, arterial restenosis, sepsis and septic shock, toxic shock syndrome, grafts vs. host reaction, allograft rejection, treatment of cytokine-mediated chronic tissue degeneration, rheumatoid arthritis, arthritis, rheumatoid spondylitis, osteoahritis, coronary insufficiency, myalgias, multiple sclerosis, malaria, AIDS, cachexia, prevention of tumor growth and tissue invasion, leukemia, depression, memory impairment and acute stroke. The compounds according to the invention are additionally suitable for reducing the damage to infarct tissue after reoxygenation.

The active component can act systemically and/or locally. For this purpose, it can be applied in a suitable manner, for example orally, parenterally, pulmonally, nasally, sublingually, lingually, buccally, rectally, transdermally, conjunctively, otically or as an implant.

For these application routes, the active component can be administered in suitable application forms.

Useful oral application forms include application forms which release the active component rapidly and/or in modified form, such as for example tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include for example inhalatory pharmaceutical forms (including powder inhalers, nebulizers), nasal drops/solutions, sprays; tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders or implants.

The active components can be converted into the recited application forms in a manner known per se. This is carried out using inert non-toxic, pharmaceutically suitable excipients. These include inter alia carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

Generally it has proved advantageous in the case of parenteral application to administer amounts of about 0.001 to 1 mg/kg and preferably about 0.01 to 0.5 mg/kg of body weight to achieve efficacious results. In the case of oral administration, the amount is about 0.001 to 50 mg/kg and preferably about 0.001 to 20 mg/kg of body weight.

In spite of this, it can be necessary in certain circumstances to depart from the amounts mentioned, namely as a function of body weight, application route, individual behaviour towards the active component, manner of preparation and time or interval at which application takes place. It can for instance be sufficient in some cases to use less than the aforementioned minimum amount, while in other cases the upper limit mentioned will have to be exceeded. In the case of the application of larger amounts, it can be advisable to divide them into a plurality of individual doses spread through the day.

The percentages in the tests and examples which follows are, unless otherwise stated, by weight; parts are by weight. Solvent ratios, dilution ratios and concentrations reported for liquid/liquid solutions are each based on the volume.

Test Descriptions

1. Preparation of human PMN

Human PMN (polymorphonuclear neutrophil leucocytes) are readily purified from peripheral blood. Phosphodiesterase in these cells is predominantly located in the membrane fraction. Inhibitory potency of compounds against this preparation correlate well with the anti-inflammatory activity as measured by inhibiton of superoxide production.

Blood was taken from healthy subjects by venous puncture and neutrophils were purified by dextran sedimentation and density gradient centrifugation on Ficoll Histopaque and resuspended in the buffered medium.

2. Assay of human PMN phosphodiesterase

This was performed as a particulate fraction from human PMN essentially as described by Souness and Scott [Biochem. J. 291, 389–395 (1993)]. Particulate fractions were treated with sodium vanadate/glutathione as described by the authors to express the discrete stereospecific site on the phosphodiesterase enzyme. The prototypical PDE 4 inhibitor, rolipram, had an $IC_{50}$ value in the range 450 nM–1500 nM, thus defining this preparation as the so-called "low affinity" [L] form. The preparation examples had $IC_{50}$ values within the range of 1 nM–1,000 nM.

3. Inhibition of FMLP-stimulated production of superoxide radical anions

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 µM, the DMSO concentration was 0.1% v/v in all wells. After addition of cytochalasin b (5 µg×ml$^{-1}$) the plate was incubated for 5 min at 37° C. Neutrophils were then stimulated by addition of $4 \times 10^{-8}$ M FMLP (N-Formyl-Met-Leu-Phe) and superoxide generation measured as superoxide dismutase inhibitable reduction of cytochrome C by monitoring the $OD_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\frac{[1 - (Rx - Rb)]}{(Ro - Rb)} \times 100$$

Rx=Rate of the well containing the compound according to the invention
   Ro=Rate in the control well
   Rb=Rate in the superoxide dismutase containing blank well 4. Assay of binding to the rolipram binding site (PDE 4 high affinity site; "H-PDE 4 form") in rat brain membranes:

The activity of compounds on the PDE 4 high affinity site ("H-PDE 4 form") is readily measured by determining their potency for displacement of [$^3$H]-rolipram from its binding site in rat brain membranes. Activity at this site is believed to be a measure of side effect potential (e.g. stimulation of stomach acid secretion, nausea and emesis).

The rolipram binding site assay was performed essentially as described by Schneider et al. [Eur. J. Pharmacol. 127, 105–115 (1986)].

5. Lipopolysaccharide (LPS)—induced neutrophil influx into rat lung

Intranasal administration of LPS to rats causes a marked influx of neutrophils into the lungs measurable by histological or biochemical (myeloperoxidase content of the cell pellet) analysis of the bronchoalveolar lavage fluid 24 h later. Rats were treated with test compound or vehicle administered by the oral route 1 h prior to and 6 h after administration of intranasal LPS. 24 hours later animals were euthanatized and their lungs lavaged with PBS (phosphate buffered saline). Neutrophil and total cell numbers were analysed.

6. Emetic potential in the marmoset

Vehicle or test compound was administered by the oral route to conscious marmosets. Animals were observed for emetic episodes or abnormal behaviour for 1 h post dosing. In some experiments, if no adverse response was seen, a separate group of animals was tested at ½ log dose higher until emesis or abnormal behaviour was observed. The highest dose at which no abnormal behavior or emetic episodes occurred was recorded as the NOEL.

Materials and Methods

LC-MS Method A

| LC-parameters: | solution A: acetonitrile<br>solution B: 0.3 g 30% HCl/L water<br>column oven 50° C.;<br>column Symmetry C18 2.1 × 150 mm | | | |
|---|---|---|---|---|
| gradient: | time [min] | % A | % B | flow [mL/min] |
| | 0 | 10 | 90 | 0.9 |
| | 3 | 90 | 10 | 1.2 |
| | 6 | 90 | 10 | 1.2 |

LC-MS Method B

| LC-parameters: | solution A: acetonitrile/0.1% formic acid solution B: water/0.1% formic acid column oven 40° C.; column Symmetry C18 2.1 × 50 mm | | | |
|---|---|---|---|---|
| gradient: | time [min] | % A | % B | flow [mL/min] |
| | 0 | 10 | 90 | 0.5 |
| | 4 | 90 | 10 | 0.5 |
| | 6 | 90 | 10 | 0.5 |
| | 6.1 | 10 | 90 | 1.0 |
| | 7.5 | 10 | 90 | 0.5 |

GC-MS Method A

| Column: | HP-5 30 m × 320 µm × 0.25 µm |
|---|---|
| Carrier Gas: | Helium |
| Mode: | Constant flow, initial flow: 1.5 mL/min |
| Oven ramp: | initial temp: 60° C. initial time: 1 min rate: 14° C./min up to 300° C., then 300° C. 2 min |

Unless specified otherwise, the following chromatographic conditions were applied: chromatography was performed on silica gel Si 60; for flash chromatography, the usual conditions were followed as described in Still, *J. Org. Chem.* 43, 2923 (1978); mixtures of dichloromethane and methanol or cyclohexane and ethylacetate were used as eluants. Unless specified otherwise, reactions were executed under an argon atmosphere and under anhydrous conditions.

Abbreviations
HPLC=high performance liquid chromatography
MS=mass spectroscopy
NMR=nuclear magnetic resonance spectroscopy
LC-MS=liquid chromatography combined with mass spectroscopy
GC-MS=gas chromatography combined with mass spectroscopy
MeOH=methanol
DMF=dimethylformamide
DMSO=dinethylsulfoxide
THF=tetrahydrofuran

STARTING MATERIALS

Example 1A 2-(Acetylamino)butanoic acid

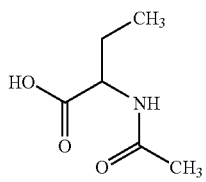

163 g (1.58 mol) 2-aminobutanoic acid are dissolved in acetic acid, and 242 g (2.37 mol) acetic anhydride are added dropwise. The mixture is stirred for 2 h at 100° C. until completion of reaction, then the solution is evaporated to dryness in vacuo. The solid residue is suspended in ethyl acetate, filtered and washed with diethyl ether.

Yield: 220 g (95.9%)

$^1$H-NMR (Methanol-d$_4$): δ=0.97 (t, 3H), 1.65–1.93 (m, 2H), 1.99 (s, 3H), 4.29 (q, 1H) ppm.

Example 2A

Ethyl 3-(acetylamino)-2-oxopentanoate

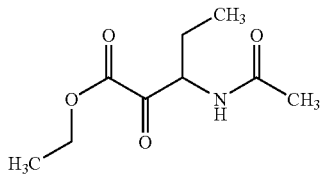

9.2 g (63.4 mmol) 2-(acetylamino)butanoic acid are suspended in 120 ml tetrahydrofuran and heated to reflux together with 15.0 g (190 mmol) pyridine and a bit of N,N-dimethylaminopyridine. While heating at reflux, 17.3 g (127 mmol) ethyl chloro(oxo)acetate are added dropwise. The reaction mixture is heated at reflux until no more evolution of gas can be observed. After cooling down to room temperature, the reaction mixture is added to ice water and the organic phase extracted with ethyl acetate. The dried organic phase is evaporated to dryness in vacuo, dissolved in ethanol and the solution directly used for the next reaction.

Example 3A

2-[(Cyclopentylcarbonyl)amino]butanoic acid

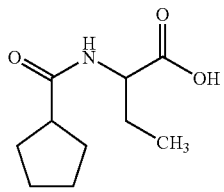

35 g (339 mmol) 2-aminobutanoic acid and 75.6 g (747 mmol) triethylamine are suspended in 300 ml of dichloromethane and stirred at 0° C. 81 g (747 mmol) chlorotrimethylsilane are added dropwise, then the mixture is stirred for 1 hour at room temperature and for 1 hour at 40° C. After cooling down to −10° C., 45 g (339 mmol) cyclopentanecarbonyl chloride are added slowly. The reaction mixture is stirred for 2 hours at −10° C. and then for 1 hour at room temperature. At 0° C., 50 ml of water are added. The mixture is diluted with water and dichloromethane, filtered and the solid product washed with water/dichloromethane 9:1, toluene and diethylether.

Yield 52.4 g (77%)

$^1$H-NMR (DMSO-d$_6$, 300 MHz): δ=0.9 (t, 3H), 1.6 (m, 10H), 2.6 (m, 1H), 4.1 (m, 2H), 7.9 (d, 1H), 12.4 (s, 1H) ppm.

Example 4A

Ethyl 3-[(cyclopentylcarbonyl)amino]-2-oxopentanoate

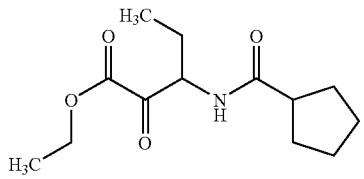

1.6 g (8 mmol) 2-[(cyclopentylcarbonyl)amino]butanoic acid are suspended in 30 ml tetrahydrofuran and heated to reflux together with 1.91 g (24 mmol) pyridine and a bit of N,N-dimethylaminopyridine. While heating at reflux, 2.19 g (16 mmol) ethyl chloro(oxo)acetate are added dropwise. The reaction mixture is heated at reflux until no more evolution of gas can be observed. After cooling down to room temperature, the reaction mixture is added to ice water and the organic phase extracted with ethyl acetate. The dried organic phase is evaporated to dryness in vacuo, dissolved in ethanol and the solution directly used for the next reaction.

Example 5A

4-Cyanobenzenecarboximidamide hydrochloride

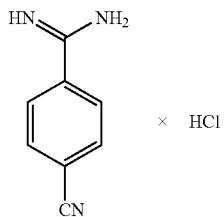

6.64 g (124 mmol, 2 equiv.) ammonium chloride are suspended in 100 ml of dry toluene under an argon atmosphere, and the mixture is cooled to 0° C. 62 ml (124 mmol, 2 equiv.) of a 2M solution of trimethylaluminium in hexane are added dropwise, and the reaction mixture is stirred at room temperature until no more evolution of gas is observed. After addition of 10.0 g (62 mmol, 1 equiv.) methyl 4-cyanobenzoate, the mixture is stirred at 80° C. bath temperature over night. It is then cooled down to 0° C., and 50 ml of methanol are added with consequent stirring for 1 hour at room temperature. After filtration, the solid is washed with methanol for several times, the solution is evaporated to dryness in vacuo and the residue washed with methanol.

Yield: 8.5 g (76%)

LC/MS (13): MS (ESI): 145 (M+H)$^+$, retention time 0.33 min.

Example 6A

3-Nitrobenzenecarboximidamide hydrochloride

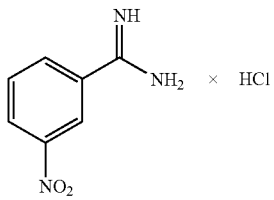

In analogy to the procedure for Example 5A, 30.0 g (203 mmol) 3-nitrobenzonitrile and proportionate amounts of the other reagents are used.

Yield: 24.5 g (47%)

LC/MS (A): retention time 0.40 min., m/z 166 [M+H]$^+$

Example 7A

Ethyl 4-{6-[1-(acetylamino)propyl]-5-oxo-4,5-dihydro-1,2,4-triazin-3-yl}benzoate

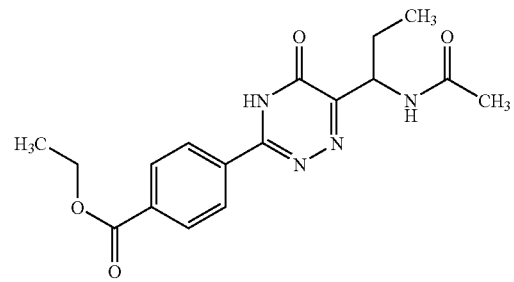

1.98 g (8.66 mmol) ethyl 4-[amino(imino)methyl]benzoate hydrochloride are suspended in 50 ml of ethanol and 1.47 g (10.2 mmol, 1.2 equiv.) hydrazine hydrate are added. After stirring at room temperature for 1 hour, 2.59 g (13 mmol, 1.5 equiv.) of the compound of Example 2A, dissolved in 10 ml of ethanol, are added. The reaction mixture is stirred at 80° C. (bath temperature) for 4 hours and then at room temperature over night. The mixture is evaporated to dryness in vacuo and the product is purified by chromatography (flash or column chromatography or preparative HPLC).

Yield: 1.42 g (48%)

$^1$H-NMR (DMSO-d$_6$, 300 MHz): δ=0.9 (t, 3H), 1.4 (t, 3H), 1.6 (m, 1H), 1.8 (m, 1H), 1.9 (s, 3H), 4.4 (q, 2H), 4.9 (m, 1H), 8.2 (m, 4H), 14.2 (br. s, 1H) ppm.

Example 8A

N-{1-[3-(4-Hydroxyphenyl)-5-oxo-4,5-dihydro-1,2,4-triazin-6-yl]propyl}acetamide

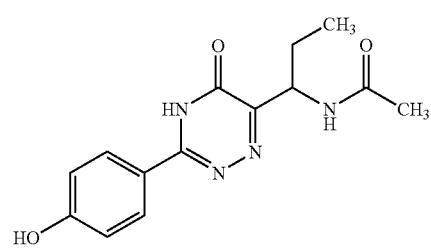

In analogy to the procedure for Example 7A, 5.0 g (29.0 mmol) 4-hydroxybenzene-carboximidamide hydrochloride and proportionate amounts of the other reagents are used.

Yield: 4.23 g (51%)

LC/MS (B): MS (ESI): 289 (M+H)$^+$, retention time 1.65 min.

Example 9A

N-{1-[3-(4-Cyanophenyl)-5-oxo-4,5-dihydro-1,2,4-triazin-6-yl]propyl}acetamide

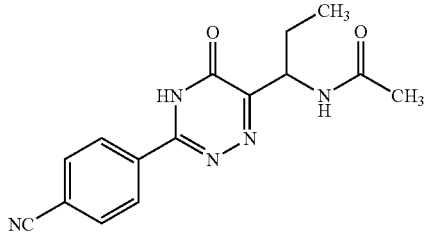

In analogy to the procedure for Example 7A, 8.4 g (46.3 mmol) of Example 5A and proportionate amounts of the other reagents are used.

Yield: 5.77 g (42%)

LC/MS (A): MS (ESI): 298 (M+H)+, retention time 1.64 min.

Example 10A

N-{1-[3-(3-Nitrophenyl)-5-oxo-4,5-dihydro-1,2,4-triazin-6-yl]propyl}acetamide

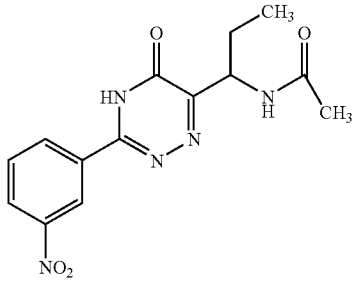

In analogy to the procedure for Example 7A, 35.0 g (174 mmol) 3-nitrobenzenecarboximidamide hydrochloride and proportionate amounts of the other reagents are used.

Yield: 13.6 g (25%)

$^1$H-NMR (200 MHz, CDCl$_3$): δ=0.97 (t, 3H), 1.83–2.08 (m, 5H, s at 2.02), 5.09 (m, 1H), 7.33 (d, 1H, NH), 7.76 (t, 1H), 8.45 (d, 1H), 8.58 (d, 1H), 9.12 (s, 1H) ppm.

Example 11A 4-(6-{1-[(Cyclopentylcarbonyl)amino]propyl}-5-oxo-4,5-dihydro-1,2,4-triazin-3-yl)-benzamide

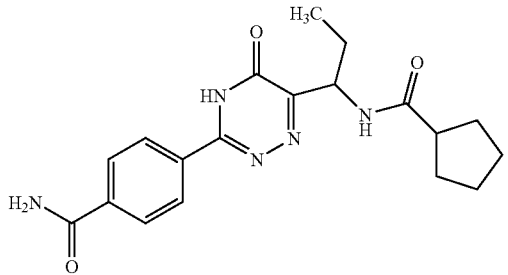

2.84 g (14.2 mmol, 1 equiv.) 4-[amino(imino)methyl]benzamide hydrochloride are suspended in 10 ml of ethanol and 1.37 g (26.8 mmol, 1.2 equiv.) hydrazine hydrate are added. After stirring at 60° C. for 1 hour, 6.28 g (24.6 mmol, 1.1 equiv.) ethyl 3-[(cyclopentylcarbonyl)-amino]-2-oxo-pentanoate (Example 4A), dissolved in 40 ml of ethanol, are added. The reaction mixture is stirred at 70° C. (bath temperature) for 4 hours. The mixture is evaporated to dryness in vacuo and the product is purified by flash chromatography.

Yield: 45 mg (1%)

LC/MS (A): MS (ESI): 369 (M+H)+, retention time 2.66 min.

Example 12A

4-[6-(1-Aminopropyl)-5-oxo-4,5-dihydro-1,2,4-triazin-3-yl]benzoic acid

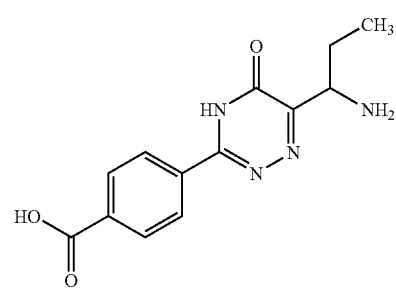

1.36 g (3.95 mmol) of Example 7A are heated to reflux in 20 ml 2 N hydrochloric acid for 18 hours. After cooling down to room temperature, the mixture is neutralized with 10% sodium hydroxide and, after addition of ethanol, evaporated to dryness in vacuo. The residue is treated with methanol and the filtrate separated from the salts. The filtrate is evaporated to dryness in vacuo and the product purified by chromatography (flash or column chromatography or preparative HPLC).

Yield: 1.12 g (quant.)

LC/MS (A): MS (ESI): 275 (M+H)+, retention time 0.45 min.

Example 13A 6-(1-Aminopropyl)-3-(4-hydroxyphenyl)-1,2,4-triazin-5(4H)-one

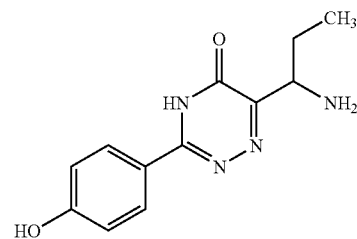

In analogy to the procedure for Example 12A, 4.22 g (14.6 mmol) of Example 8A and proportionate amounts of the other reagents are used. The product is used in the next step without further purification.

LC/MS (3): MS (ESI): 247 (M+H)+, retention time 0.35 min.

Example 14A

4-[6-(1-Aminopropyl)-5-oxo-4,5-dihydro-1,2,4-triazin-3-yl]benzonitrile

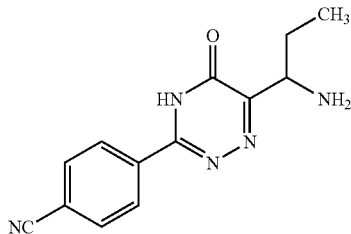

In analogy to the procedure for Example 12A, 5.70 g (19.2 mmol) of Example 9A and proportionate amounts of the other reagents are used.

LC/MS (A): MS (ESI): 256 (M+H)$^+$, retention time 0.49 min.

Example 15A 6-(1-Aminopropyl)-3-(3-nitrophenyl)-1,2,4-triazin-5(4H)-one

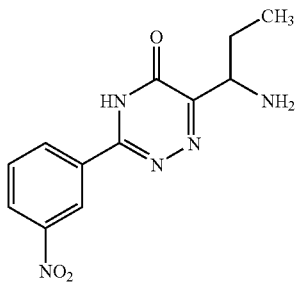

In analogy to the procedure for Example 12A, 13.5 g (42.5 mmol) N-{1-[3-(3-nitrophenyl)-5-oxo-4,5-dihydro-1,2,4-triazin-6-yl]propyl}acetamide (example 10A) and proportionate amounts of the other reagents are used.

Yield: 6.2 g (41%)

LC/MS (A): retention time 0.497 min., m/z 276 [M+H]$^+$

Example 16A 4-(6-{1-[(Cyclobutylcarbonyl)amino]propyl}-5-oxo-4,5-dihydro-1,2,4-triazin-3-yl)benzoic acid

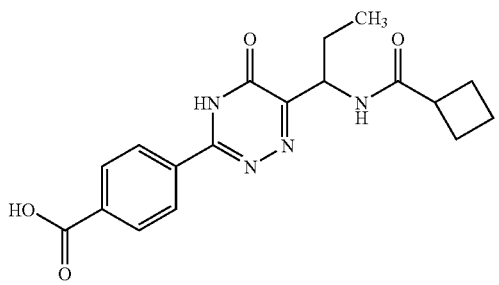

584 mg (2.13 mmol) of Example 12A are suspended in 10 ml dichloromethane, 431 mg (4.26 mmol, 2 equiv.) triethylamine and 252 mg (2.13 mmol, 1 equiv.) cyclobutanecarbonyl chloride are added. The reaction mixture is stirred at room temperature until completion of reaction (1–2 hours). The reaction mixture is added to the same volume of 1N hydrochloric acid, the organic phase is washed with 1N hydrochloric acid and brine, dried over sodium sulfate and evaporated to dryness. The product is used without further purification or purified by chromatography (flash or column chromatography or preparative HPLC).

Yield: 106 mg (14%)

$^1$H-NMR (DMSO-d$_6$, 300 MHz): δ=0.9 (t, 3H), 1.6 (m, 1H), 1.8 (m, 3H), 2.0 (m, 2H), 2.1 (m, 2H), 3.1 (m, 1H), 4.9 (m, 1H), 7.9 (d, 1H), 8.1 (m, 4H), 13.5 (br, 1H), 14.2 (br, 1H) ppm.

Example 17A 4-(6-{1-[(Cyclopentylcarbonyl)amino]propyl}-5-oxo-4,5-dihydro-1,2,4-triazin-3-yl)benzoic acid

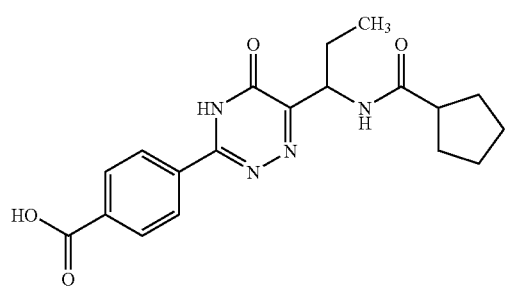

In analogy to the procedure for Example 16A, 550 mg (2.01 mmol) of Example 12A, 266 mg (2.01 mmol) cyclopentanecarbonyl chloride and proportionate amounts of the other reagents are used.

Yield: 211 mg (28%)

LC/MS (B): MS (ESI): 371 (M+)$^+$, retention time 2.93 min.

Example 18A

N-{1-[3-(4-Hydroxyphenyl)-5-oxo-4,5-dihydro-1,2,4-triazin-6-yl]propyl}cyclo-pentanecarboxamide

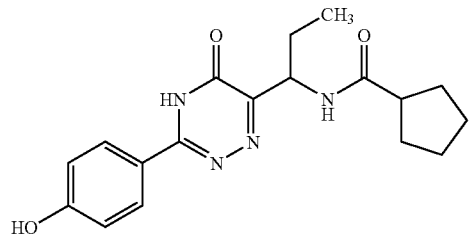

In analogy to the procedure for Example 16A, 200 mg (0.81 mmol) of Example 13A, 102 mg (0.89 mmol) cyclopentanecarbonyl chloride and proportionate amounts of the other reagents are used.

Yield: 24 mg (28%)

LC/MS (A): MS (ESI): 343 (M+H)$^+$, retention time 2.00 min.

Example 19A

N-{1-[3-(3-Nitrophenyl)-5-oxo-4,5-dihydro-1,2,4-triazin-6-yl]propyl}cyclopentane-carboxamide

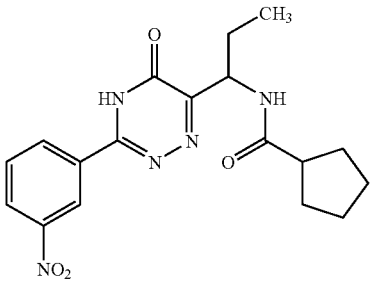

In analogy to the procedure for Example 16A, 3.0 g (10.9 mmol) 6-(1-aminopropyl)-3-(3-nitrophenyl)-1,2,4-triazin-5 (4H)-one (Example 15A), 2.2 g (16.3 mmol) cyclopentanecarbonyl chloride and proportionate amounts of the other reagents are used.

Yield: 3.9 g (93%)

$^1$H-NMR (200 MHz, CDCl$_3$): δ=0.91 (t, 3H), 1.54–2.09 (m, 10H), 2.71 (quint, 1H), 5.25 (m, 1H), 7.59 (m, NH), 7.74 (t, 1H), 8.48 (d, 1H), 8.64 (d, 1H), 9.25 (s, 1H) ppm.

Example 20A cis-4-tert-Butyl-N-{1-[3-(3-nitrophenyl)-5-oxo-4,5-dihydro-1,2,4-triazin-6-yl]-propyl}cyclohexanecarboxamide

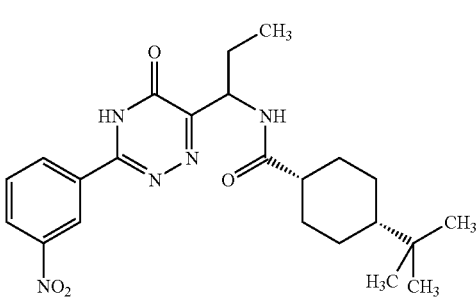

In analogy to the procedure for Example 16A, 3.2 g (11.6 mmol) 6-(1-aminopropyl)-3-(3-nitrophenyl)-1,2,4-triazin-5 (4H)-one (Example 15A), 2.4 g (11.6 mmol) cis-4-tert.-butylcyclohexanecarbonyl chloride (Example 42A) and proportionate amounts of the other reagents are used. The crude product is used in the next step without further purification.

Yield: 5.1 g (crude)

Example 21A

7-Cyclopentyl-5-ethyl-2-(3-nitrophenyl)imidazo[5,1-f][1,2,4]triazin-4(3H)-one

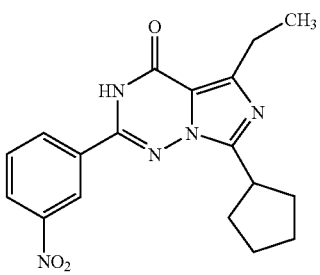

3.5 g (9.4 mmol) N-{1-[3-(3-nitrophenyl)-5-oxo-4,5-dihydro-1,2,4-triazin-6-yl]propyl}-cyclopentanecarboxamide (Example 19A) are suspended in 60 ml dichloroethane, and 1.45 g (9.4 mmol) phosphoroxychloride are added. The mixture is stirred at reflux for 3 hour. After cooling down to 0° C., 10 ml saturated NaHCO$_3$ (aq) is added dropwise. The mixture is stirred for about 20 min at room temperature and then evaporated to dryness in vacuo. The product is purified by chromatography (flash or column chromatography).

Yield: 1.8 g (54%)

$^1$H-NMR (200 MHz, CDCl$_3$): δ=1.33 (t, 3H), 1.63–2.22 (m, 8H), 3.03 (q, 2H), 3.68 (quin., 1H), 7.76 (t, 1H), 8.38–8.48 (m, 2H), 8.89–8.95 (s, 1H), 10.85 (s, 1H, NH) ppm.

Example 22A 7-(4-tert-Butylcyclohexyl)-5-ethyl-2-(3-nitrophenyl)imidazo[5,1-f][1,2,4]triazin-4(3H)-one

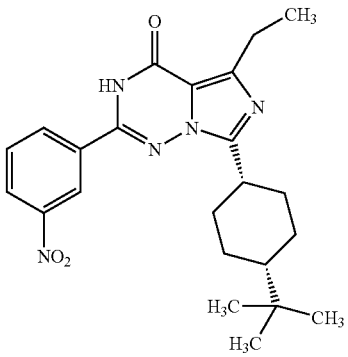

In analogy to the procedure for Example 21A, 5.1 g (11.6 mmol) crude cis-4-tert-butyl-N-{1-[3-(3-nitrophenyl)-5-oxo-4,5-dihydro-1,2,4-triazin-6-yl]propyl}cyclo-hexanecarboxamide (Example 20A), 2.7 g (17.4 mmol) phosphoric trichloride are stirred at reflux for 3 hours and proportionate amounts of the solvents are used.

Yield: 3.0 g (61%)

Example 23A cis-4-[7-(4-tert-Butylcyclohexyl)-5-ethyl-4-oxo-3,4-dihydroimidazo[5,1-f][1,2,4]-triazin-2-yl]benzonitrile

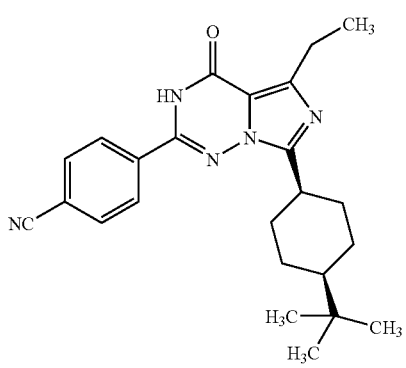

900 mg (3.53 mmol) of Example 14A are suspended in 50 ml dichloroethane, and 535 mg (5.3 mmol) triethylamine and 715 mg (3.53 mmol) cis-4-tert-butylcyclohexyl-carbonyl chloride (Example 42A) are added. The mixture is stirred at room temperature for one hour, then 811 mg (5.29 mmol) phosphoroxychloride are added. The mixture is stirred at reflux for 3 hours. After cooling down to room temperature, ethyl acetate and saturated NaHCO₃ (aq) are added. The organic phase is washed with saturated NaHCO₃ (aq), water and brine, dried over sodium sulfate and evaporated to dryness in vacuo. The product is purified by chromatography (flash or column chromatography or preparative HPLC).

Yield: 529 mg (37%)

$^1$H-NMR (DMSO-$d_6$, 200 MHz): δ=0.8 (s, 9H), 1.1 (m, 1H), 1.2 (t, 3H), 1.5–1.7 (m, 6H), 2.2 (m, 2H), 2.9 (t, 2H), 3.6 (m, 1H), 8.0 (m, 1H), 8.1 (m, 1H), 12.0 (s, 1H) ppm.

Example 24A

N-{1-[3-(3-Bromophenyl)-5-oxo-4,5-dihydro-1,2,4-triazin-6-yl]propyl}acetamide

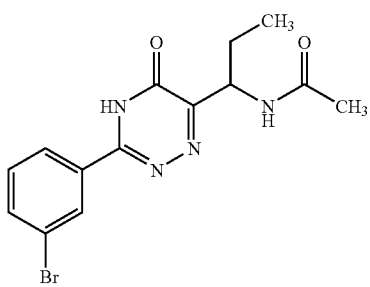

2.02 g (8.6 mmol, 1 equiv.) 3-bromobenzenecarboximidamide hydrochloride (Example 31A) are suspended in 50 ml of ethanol, and 1.47 g (10.2 mmol, 1.2 equiv.) hydrazine hydrate are added. After stirring at room temperature for 1 hour, 2.59 g (13 mmol, 1.5 equiv.) of the compound of Example 2A, dissolved in 10 l of ethanol, are added. The reaction mixture is stirred at 80° C. (bath temperature) for 4 hours and then at room temperature over night. The mixture is evaporated to dryness in vacuo and the product is purified by chromatography (flash or column chromatography or preparative HPLC).

Yield: 758 mg (25%)

$^1$H-NMR (DMSO-$d_6$, 200 MHz): δ=0.9 (t, 3H), 1.6 (m, 1H), 1.8 (m, 1H), 1.9 (s, 3H), 4.9 (m, 1H), 7.5 (m, 1H), 7.8 (m, 1H), 8.0 (m, 1H), 8.2 (m, 2H), 14.1 (br. s, 1H) ppm.

Example 25A 6-(1-Aminopropyl)-3-(3-bromophenyl)-1,2,4-triazin-5(4H)-one

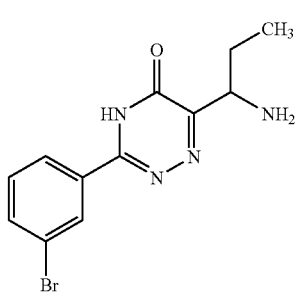

749 mg (2.13 mmol) of Example 24A are heated to reflux in 20 ml 2 N hydrochloric acid for 18 hours. After cooling down to room temperature, the mixture is neutralized with 10% sodium hydroxide and, after addition of ethanol, evaporated to dryness in vacuo. The residue is treated with methanol and the filtrate separated from the salts. The filtrate is evaporated to dryness in vacuo and the product purified by chromatography (flash or column chromatography or preparative HPLC).

Yield: 320 mg (49%)

$^1$H-NMR (DMSO-$d_6$, 200 MHz): δ=0.9 (t, 3H), 1.9 (m, 2H), 4.3 (dd, 1H), 7.4 (m, 1H), 7.6 (m, 1H), 8.1 (br. s, 2H), 8.2 (m, 1H), 8.4 (m, 1H) ppm.

Example 26A

N-{1-[3-(3-Bromophenyl)-5-oxo-4,5-dihydro-1,2,4-triazin-6-yl]propyl}-4-tert-butyl-cyclohexanecarboxamide

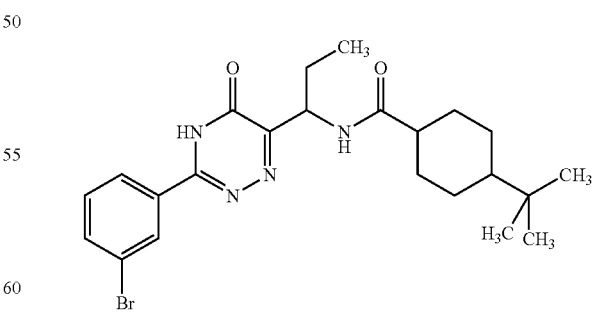

500 mg (1.62 mmol, 1 equiv.) of Example 25A are suspended in 40 ml dichloromethane, 0.48 ml (3.44 mmol, 2 equiv.) triethylamine and 328 mg (1.62 mmol) 4-tert-butylcyclohexanecarbonyl chloride are added. The reaction mixture is stirred at room temperature until completion of reaction (1–2 hours). The reaction mixture is added to the same volume of 1N hydrochloric acid, the organic phase is washed with 1N hydrochloric acid and brine, dried over sodium sulfate and evaporated to dryness. The product is used without further purification or purified by chromatography (flash or column chromatography or preparative HPLC).

LC/MS (A): MS (ESI): 475, 477 (M+H)+, retention time 3.17, 3.20 min.

Example 27A 2-(3-Bromophenyl)-7-(4-tert-butylcyclohexyl)-5-ethylimidazo[5,1-f][1,2,4]triazin-4(3H)-one

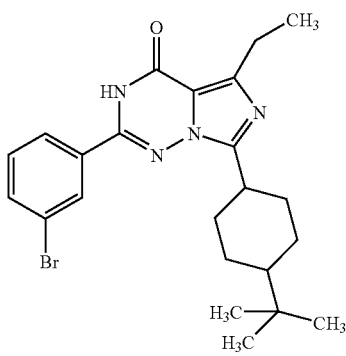

770 mg (1.62 mmol, 1 equiv.) of Example 26A are suspended in 70 ml dichloroethane, and 373 mg (2.45 mmol, 1.5 equiv.) phosphoroxychloride are added. The mixture is stirred at reflux for 3 hours. Then another 373 mg of phosphoric trichloride are added, and stirring at reflux is continued over night. After cooling down to room temperature, ethyl acetate and saturated $NaHCO_3$ (aq) are added. The organic phase is washed with saturated $NaHCO_3$ (aq), water and brine, dried over sodium sulfate and evaporated to dryness in vacuo. The product is purified and the isomers are separated by chromatography (flash or column chromatography or preparative HPLC).

Yield: 156 mg (21%) cis-isomer $^1$H-NMR (DMSO-$d_6$, 300 MHz): δ=0.8 (s, 9H), 1.1 (m, 2H), 1.2 (t, 3H), 1.5 (m, 2H), 1.7 (m, 2H), 2.2 (m, 2H), 2.9 (q, 2H), 3.5 (m, 1H), 7.5 (m, 1H), 7.8 (m, 1H), 8.0 (m, 1H), 8.1 (m, 1H), 11.8 (s, 1H) ppm.

Example 28A

N-{1-[3-(4-Bromophenyl)-5-oxo-4,5-dihydro-1,2,4-triazin-6-yl]propyl}acetamide

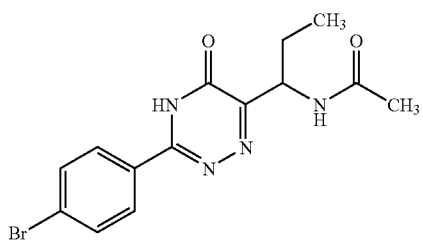

In analogy to the procedure for Example 24A, 10.2 g (43.3 mmol) 4-bromobenzene-carboximidamide hydrochloride and proportionate amounts of the other reagents are used.

Yield: 5.23 g (34%)

$^1$H-NMR (400 MHz, $CD_3OD$): δ=1.01 (t, 3H), 1.66–1.79 (m, 1H), 1.91–2.06 (m, 4H, s at 1.99), 5.02–5.09 (m, 1H), 7.75 (d, 2H), 7.93 (d, 2H) ppm.

Example 29A 6-(1-Aminopropyl)-3-(4-bromophenyl)-1,2,4-triazin-5(4H)-one

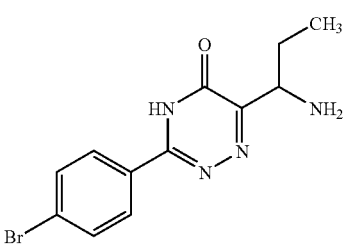

In analogy to the procedure for Example 25A, 5.0 g (14.2 mmol) N-{1-[3-(4-bromophenyl)-5-oxo-4,5-dihydro-1,2,4-triazin-6-yl]propyl}acetamide (Example 28A) and proportionate amounts of the other reagents are used.

Yield: 3.4 g (77%)

$^1$H-NMR (300 MHz, $CD_3OD$): δ=1.02 (t, 3H), 1.87–2.22 (m, 5H, s at 1.96), 4.42–4.53 (t, 1H), 7.63 (d, 2H), 8.09 (d, 2H) ppm.

Example 30A cis-2-(4-Bromophenyl)-7-(4-tert-butylcyclohexyl)-5-ethylimidazo[5,1-f][1,2,4]-triazin-4(3H)-one

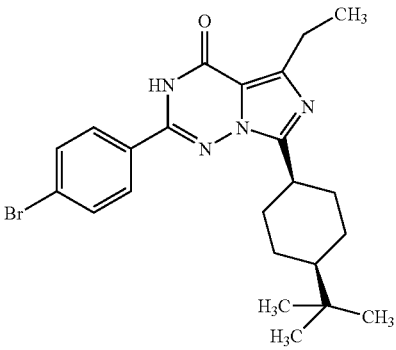

In analogy to the procedure for Example 23A, 7.6 g (24.6 mmol) 6-(1-aminopropyl)-3-(4-bromophenyl)-1,2,4-triazin-5(4H)-one (Example 29A), 4.98 g (24.55 mmol) cis-4-tert-butylcyclohexylcarbonyl chloride (Example 42A) and proportionate amounts of the other reagents are used.

Yield: 7.89 g (70%)

$^1$H-NMR (DMSO-$d_6$, 300 MHz): δ=0.8 (s, 9H), 1.1 (m, 1H), 1.2 (t, 3H), 1.5–1.7 (m, 6H), 2.2 (m, 2H), 2.9 (q, 2H), 3.6 (m, 3H), 7.7 (m, 2H), 7.9 (m, 2H) ppm.

Example 31A

3-Bromobenzenecarboximidamide hydrochloride

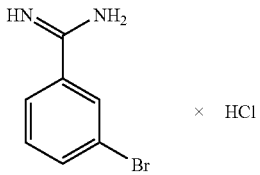

1.18 g (22 mmol, 2 equiv.) ammonium chloride are suspended in 40 ml of dry toluene under an argon atmosphere, and the mixture is cooled to 0° C. 11 ml (22 mmol, 2 equiv.) of a 2M solution of trimethylaluminium in hexane are added dropwise, and the reaction mixture is stirred at room temperature until no more evolution of gas is observed. After addition of 2.0 g (11 mmol, 1 equiv.) 3-bromobenzonitrile, the mixture is stirred at 80° C. bath temperature over night. It is then cooled down to 0° C., and 50 ml of methanol are added with subsequent stirring for 1 hour at room temperature. After filtration, the solid is washed with methanol for several times, the solution is evaporated to dryness in vacuo and the residue washed with methanol.

Yield: 2.02 g (78%)

$^1$H-NMR (DMSO-$d_6$, 300 MHz): δ=7.6 (m, 1H), 7.8 (m, 1H), 8.0 (m, 1H), 8.1 (s, 1H) ppm.

Example 32A

4-Nitrobenzenecarboximidamide hydrochloride

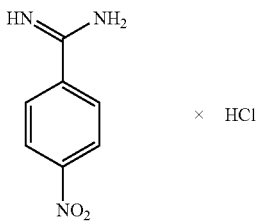

In analogy to the procedure for Example 31A, 10.0 g (67.5 mmol) 4-nitrobenzonitrile and proportionate amounts of the other reagents are used.

Yield: 12.64 g (93%)

$^1$H-NMR (DMSO-$d_6$, 200 MHz): δ=8.1 (m, 2H), 8.4 (m, 2H) ppm.

Example 33A

N-{1-[3-(4-Nitrophenyl)-5-oxo-4,5-dihydro-1,2,4-triazin-6-yl]propyl}acetamide

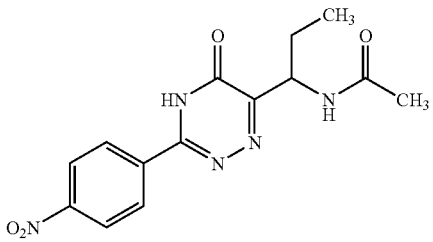

In analogy to the procedure for Example 24A, 7.29 g (36.16 mmol) of Example 32A and proportionate amounts of the other reagents are used.

Yield: 3.35 g (29%)

$^1$H-NMR (DMSO-$d_6$, 400 MHz): δ=0.9 (t, 3H), 1.6 (m, 1H), 1.9 (m, 1H; s, 3H), 5.0 (m, 1H), 8.1 (d, 1H), 8.3 (m, 2H), 8.4 (m, 2H) ppm.

Example 34A 6-(1-Aminopropyl)-3-(4-nitrophenyl)-1,2,4-triazin-5(4H)-one

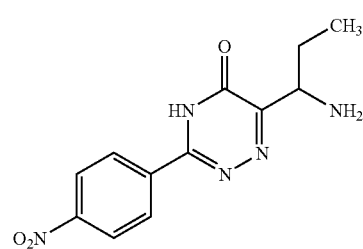

In analogy to the procedure for Example 25A, 3.33 g (10.51 mmol) of Example 33A and proportionate amounts of the other reagents are used.

Yield: 1.29 g (45%)

LC/MS (A): MS (ESI): 276 (M+H)$^+$, retention time 0.49 min.

Example 35A cis-7-(4-tert-Butylcyclohexyl)-4-chloro-5-ethyl-2-(4-nitrophenyl)imidazo[5,1-f]-[1,2,4]triazine

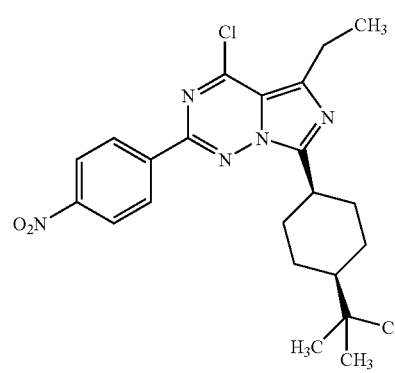

500 mg (1.82 mmol) of Example 34A are suspended in 20 ml dichloroethane, and 276 mg (2.72 mmol) triethylamine and 552 mg (2.72 mmol) cis-4-tert-butylcyclohexanecarbonyl chloride (Example 42A) are added. The mixture is stirred at room temperature for one hour, then 279 mg (1.82 mmol) phosphoroxychloride are added. The mixture is stirred at reflux for 3 hours. After cooling down to room temperature, ethyl acetate and saturated NaHCO$_3$ (aq) are added. The organic phase is washed with saturated NaHCO$_3$ (aq), water and brine, dried over sodium sulfate and evaporated to dryness in vacuo. The product is purified by chromatography.

Yield: 127 mg (16%) cis-product

MS (ESI): 442, 444 (M+H$^+$).

Example 36A 7-(cis-4-tert-Butylcyclohexyl)-5-ethyl-2-(4-nitrophenyl)imidazo[5,1-f][1,2,4]triazin-4(3H)-one

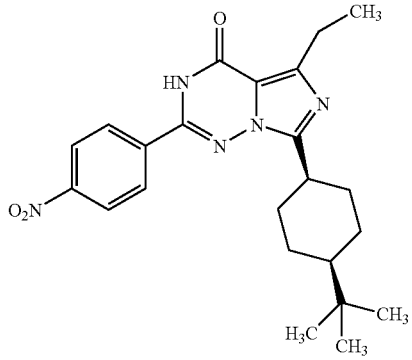

598 mg (1.35 mmol) of Example 35A are suspended in methanol, and 10 ml sodium hydroxide (10% in water) are added. The mixture is stirred at reflux over night. After cooling down to room temperature, the methanol is evaporated in vacuo, the residue dissolved in ethyl acetate, the organic phase washed with water and brine, dried over sodium sulfate and evaporated to dryness in vacuo.

Yield: 580 mg (quant.)

$^1$H-NMR (DMSO-$d_6$, 300 MHz): δ=0.8 (s, 9H), 1.1 (m, 1H), 1.2 (t, 3H), 1.5–1.7 (m, 6H), 2.2 (m, 2H), 2.9 (q, 2H), 3.6 (m, 1H), 8.2 (m, 2H), 8.4 (m, 2H), 12.1 (s, 1H) ppm.

Example 37A

3-Cyanobenzenecarboximidamide hydrochloride

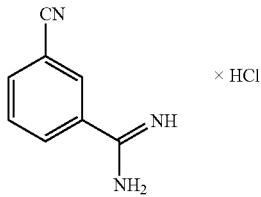

In analogy to the procedure for Example 31A, 20.0 g (125.9 mmol) 3-cyanobenzoic acid and proportionate amounts of the other reagents are used.

Yield: 4.27 g (17%)

$^1$H-NMR (DMSO-$d_6$, 300 MHz): δ=7.8 (m, 1H), 8.1 (m, 1H), 8.2 (m, 1H), 8.3 (m, 1H), 9.4 (br. s, 4H) ppm.

Example 38A

N-{1-[3-(3-Cyanophenyl)-5-oxo-4,5-dihydro-1,2,4-triazin-6-yl]propyl}acetamide

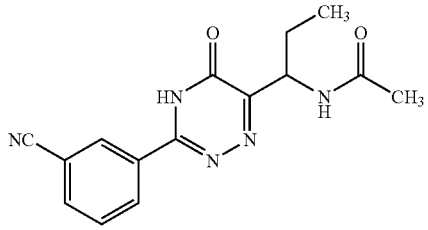

In analogy to the procedure for Example 24A, 4.27 g (23.5 mmol) of Example 37A and proportionate amounts of the other reagents are used.

Yield: 2.41 g (34%)

$^1$H-NMR (DMSO-$d_6$, 300 MHz): δ=0.9 (t, 3H), 1.6 (m, 1H), 1.9 (m, 1H; s, 3H), 4.9 (m, 1H), 7.8 (m, 1H), 8.1 (m, 2H), 8.3 (m, 1H), 8.4 (m, 1H), 14.2 (br. s, 1H) ppm.

Example 39A

3-[6-(1-Aminopropyl)-5-oxo-4,5-dihydro-1,2,4-triazin-3-yl]benzonitrile

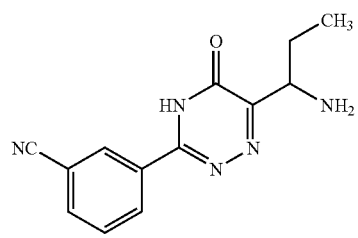

In analogy to the procedure for Example 25A, 2.41 g (8.11 mmol) of Example 38A and proportionate amounts of the other reagents are used.

Yield: 1.1 g (53%)

LC/MS (A): MS (ESI): 256 (M+H)$^+$, retention time 1.27 min.

Example 40A cis-3-[7-(4-tert-Butylcyclohexyl)-5-ethyl-4-oxo-3,4-dihydroimidazo[5,1-f][1,2,4]-triazin-2-yl]benzonitrile

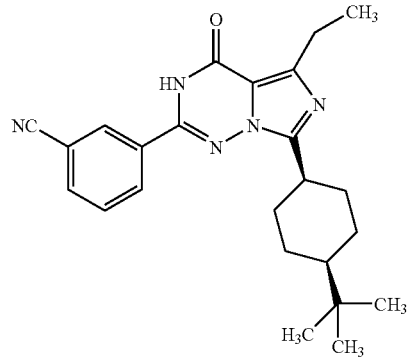

In analogy to the procedure for Example 23A, 1.09 g (4.27 mmol) of Example 39A, 0.86 g (4.27 mmol) cis-4-tert-butylcyclohexanecarbonyl chloride (Example 42A) and proportionate amounts of the other reagents are used.

Yield: 0.70 g (41%)

$^1$H-NMR (DMSO-$d_6$, 300 MHz): δ=0.8 (s, 9H), 1.1 (m, 1H), 1.2 (t, 3H), 1.5–1.7 (m, 6H), 2.2 (m, 2H), 2.9 (q, 2H), 3.6 (m, 1H), 7.7 (m, 1H), 8.0 (m, 1H), 8.3 (m, 1H), 8.4 (m, 1H), 11.9 (s, 1H) ppm.

Example 41A cis- and trans-4-tert-Butylcyclohexanecarboxylic acid

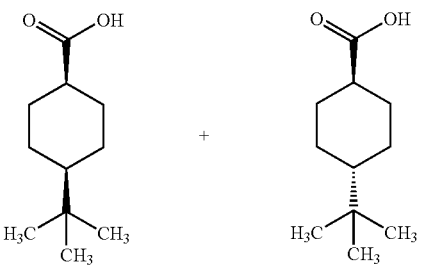

A preparative HPLC separation of cis- and trans-4-tert-butylcyclohexanecarboxylic acid was carried out under the following conditions:

| | |
|---|---|
| Feed: | 10 g isomeric mixture of cis- and trans-4-tert-butyl-cyclo-hexanecarboxylic acid dissolved in 500 ml iso-hexane (80%)/tert-butylmethylether (20%) |
| Column: | 330 × 100 mm; Self Packing Device NW 100; Merck |
| Stationary phase: | LiChrospher Si 60, 12 μm, Merck |
| Mobile phase: | iso-hexane/tert-butylmethylether (4/1 v/v) + 0.25 vol-% acetic acid |
| Flow: | 150 ml/min |
| Injection volume: | 70 ml (=1.4 g compound) |
| Wave length: | 210 nm |
| Temperature: | 25° C. |

The sample run on this column was repeatedly injected every 30 minutes. The cis-isomer is the first eluting compound.

cis-isomer:
mp.: 118° C.
$^1$H-NMR (300 MHz, DMSO): δ=0.9 (t, 3H), 1.0 (m, 3H), 1.4 (m, 2H), 1.6 (m, 1H), 2.1 (m, 2H), 2.5 (m, 1H), 12.0 (s, 1H) ppm.

trans-isomer:
mp.: 172° C.
$^1$H-NMR (300 MHz, DMSO): δ=0.9 (t, 3H), 1.0 (m, 3H), 1.3 (m, 2H), 1.7 (m, 1H), 1.9 (m, 2H), 2.1 (m, 1H), 11.9 (s, 1H) ppm.

Example 42A cis-4-tert-Butylcyclohexanecarbonyl chloride

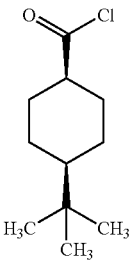

2.0 g (10.85 mmol) cis-4-tert-Butylcyclohexanecarboxylic acid are dissolved in 50 ml dichloromethane, 1.65 g (13.02 mmol) ethanedioyl dichloride are added and the solution is stirred at room temperature for one hour. The mixture is then stirred at reflux for two hours and, after cooling down to room temperature, evaporated to dryness in vacuo. The residue is then dissolved in toluene two times and again evaporated to dryness in vacuo. The residue is used in the next step without further purification.

Example 43A trans-4-tert-Butylcyclohexanecarbonyl chloride

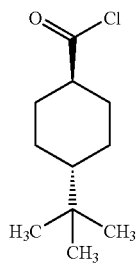

11.0 g (59.7 mmol) trans-4-tert-Butylcyclohexanecarboxylic acid are dissolved in 400 ml dichloromethane plus a few drops of DMF, 9.09 g (71.6 mmol) ethanedioyl dichloride are added and the solution is stirred at room temperature for one hour. The mixture is then stirred at reflux for two hours and, after cooling down to room temperature, evaporated to dryness in vacuo. The residue is then dissolved in toluene two times and again evaporated to dryness in vacuo. The residue is used in the next step without further purification.

PREPARATION EXAMPLES

Example 1

4-(7-Cyclobutyl-5-ethyl-4-oxo-3,4-dihydroimidazo[5,1-f][1,2,4]triazin-2-yl)benzoic acid

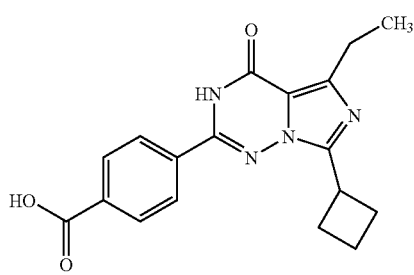

175 mg (0.49 mmol, 1 equiv.) of Example 16A are suspended in 10 ml dichloroethane, and 113 mg (0.74 mmol, 1.5 equiv.) phosphoroxychloride are added. The mixture is stirred at reflux for 3 hours. After cooling down to room temperature, ethyl acetate and saturated NaHCO$_3$ (aq) are added. The organic phase is washed with saturated NaHCO$_3$ (aq), water and brine, dried over sodium sulfate and evaporated to dryness in vacuo. The product is purified by chromatography (flash or column chromatography or preparative HPLC).

Yield: 42 mg (25%)
$^1$H-NMR (DMSO-d$_6$, 200 MHz): δ=0.9 (t, 3H), 1.9 (m, 1H), 2.1 (m, 2H), 2.3 (m, 2H), 2.4 (m, 1H), 2.9 (q, 2H), 4.0 (m, 1H), 7.9 (m, 4H) ppm.

Example 2

4-(7-Cyclopentyl-5-ethyl-4-oxo-3,4-dihydroimidazo[5,1-f][1,2,4]triazin-2-yl)benzoic acid

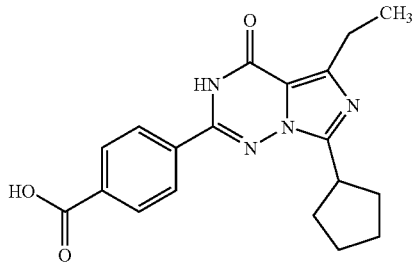

In analogy to the procedure for Example 1, 205 mg (0.55 mmol) of Example 17A, 127 mg (0.83 mmol) phosphoric trichloride are stirred at reflux for 3 hours and proportionate amounts of the solvents are used.

Yield: 135 mg (69%)

$^1$H-NMR (DMSO-$d_6$, 200 MHz): δ=0.9 (t, 3H), 1.6–1.9 (m, 6H), 2.1 (m, 2H), 3.0 (q, 2H), 3.7 (m, 1H), 8.1 (m, 4H), 12.3 (s, 1H) ppm.

Example 3

4-(7-Cyclopentyl-5-ethyl-4-oxo-3,4-dihydroimidazo[5,1-f][1,2,4]triazin-2-yl)-N-propylbenzamide

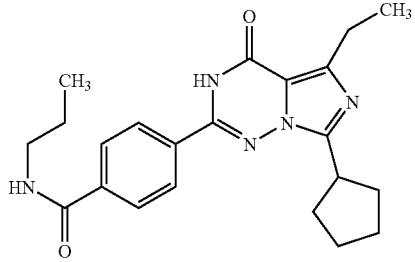

40 mg (0.11 mmol) of Example 2 are dissolved in dimethylformamide, 7.4 mg (0.12 mmol) n-propylamine, 17 mg (0.11 mmol) 1-hydroxy-1H-benzotriazole hydrate and 14 mg (0.11 mmol) 4-dimethylaminopyridine are added. The reaction mixture is stirred at 0° C., then 24 mg (0.12 mmol) 1-(3-dimethylaminopropyl)-3-ethylcarbodiimide hydrochloride are added. The mixture is stirred at room temperature for 18 hours, water is added and the resulting solid product is filtered.

Yield: 27 mg (61%)

$^1$H-NMR (DMSO-$d_6$, 200 MHz): δ=0.9 (t, 3H), 1.2 (t, 3H), 1.6 (m, 2H), 1.7–1.9 (m, 6H), 2.1 (m, 2H), 2.9 (q, 2H), 3.2 (m, 2H), 3.6 (m, 1H), 8.0 (m, 4H), 8.6 (br. t, 1H), 11.9 (s, 1H) ppm.

Example 4

4-(7-Cyclopentyl-5-ethyl-4-oxo-3,4-dihydroimidazo[5,1-f][1,2,4]triazin-2-yl)-N-phenylbenzamide

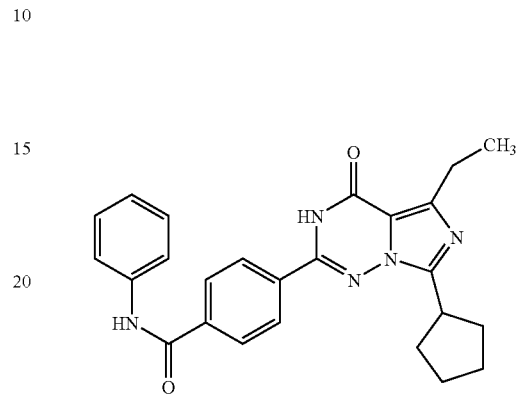

In analogy to the procedure for Example 3, 40 mg (0.11 mmol) of Example 2, 12 mg (0.12 mmol) aniline and proportionate amounts of the other reagents are used.

Yield: 20 mg (42%)

$^1$H-NMR (DMSO-$d_6$, 200 MHz): δ=0.9 (t, 3H), 1.7–1.9 (m, 6H), 2.1 (m, 2H), 2.9 (q, 2H), 3.6 (m, 1H), 7.1 (m, 1H), 7.4 (m, 2H), 7.8 (m, 2H), 8.1 (m, 4H), 10.4 (s, 1H), 12.0 (s, 1H) ppm.

Example 5

7-Cyclopentyl-5-ethyl-2-(4-hydroxyphenyl)imidazo[5,1-f][1,2,4]triazin-4(3H)-one

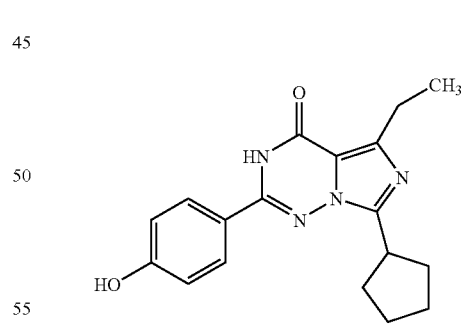

In analogy to the procedure for Example 1, 20 mg (0.06 mmol) of Example 18A, 13 mg (0.09 mmol) phosphoric trichloride are stirred at reflux for 3 hours and proportionate amounts of the solvents are used.

Yield: 9 mg (48%)

$^1$H-NMR (DMSO-$d_6$, 200 MHz): δ=0.9 (t, 3H), 1.6 (m, 2H), 1.8 (m, 4H), 2.1 (m, 2H), 3.0 (q, 2H), 3.6 (m, 1H), 6.9 (m, 2H), 7.9 (m, 2H), 10.1 (s, 1H), 11.6 (s, 1H) ppm.

Example 6 cis-2-(4-Aminophenyl)-7-(4-tert-butylcyclohexyl)-5-ethylimidazo[5,1-f][1,2,4]triazin-4(3H)-one

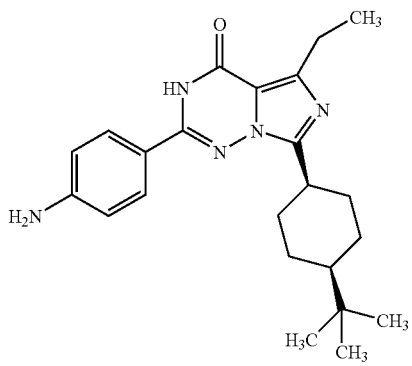

580 mg (1.37 mmol) cis-7-(4-tert-butylcyclohexyl)-5-ethyl-2-(4-nitrophenyl)imidazo[5,1-f][1,2,4]triazin-4(3H)-one (Example 36A) are dissolved in 50 ml tetrahydrofuran and catalytic amounts of palladium (10% on charcoal) are added. The mixture is stirred for 18 hour at room temperature in a 3 bar hydrogen atmosphere. Then the mixture is filtrated and the organic phase evaporated to dryness in vacuo.

Yield: 433 mg (80%)

$^1$H-NMR (DMSO-$d_6$, 200 MHz): δ=0.8 (s, 9H), 1.1 (m, 1H), 1.2 (t, 3H), 1.5–1.7 (m, 6H), 2.2 (m, 2H), 2.4 (q, 2H), 3.5 (m, 1H), 5.7 (s, 2H), 6.6 (m, 2H), 7.7 (m, 2H), 11.4 (s, 1H) ppm.

Example 7 cis-N-{4-[7-(4-tert-Butylcyclohexyl)-5-ethyl-4-oxo-3,4-dihydroimidazo[5,1-f]-[1,2,4]triazin-2-yl]phenyl}acetamide

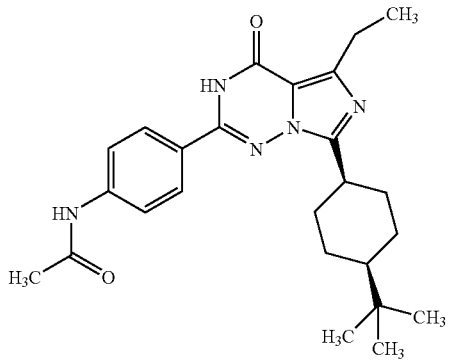

In analogy to the procedure for Example 3, 50 mg (0.13 mmol) of Example 6, 8 mg (0.14 mmol) acetic acid and proportionate amounts of the other reagents are used.

Yield: 7 mg (12%)

LC/MS (A): MS (ESI): 436 (M+H)$^+$, retention time 2.75 min.

Example 8 cis-7-(4-tert-Butylcyclohexyl)-2-{4-[(cyclohexylmethyl)amino]phenyl}-5-ethylimidazo[5,1-f][1,2,4]triazin-4(3H)-one

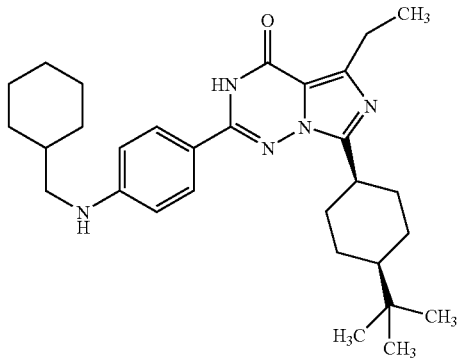

35 mg (0.09 mmol) of Example 6 are dissolved in 5 ml methanol, 20 mg (0.18 mmol) cyclohexanecarbaldehyde and 6 mg (0.09 mmol) sodium cyanoborohydride are added. The reaction mixture is stirred at room temperature for 2 hours and quenched with 2 N hydrochloric acid. The methanol is evaporated in vacuo and dichloromethane is added to the aqueous residue. The organic phase is dried over sodium sulfate, evaporated to dryness in vacuo, triturated with diethyl ether and the solid product is isolated.

Yield: 30 mg (69%)

$^1$H-NMR (DMSO-$d_6$, 200 MHz): δ=0.8 (s, 9H), 1.0 (m, 1H), 1.2 (m, 4H), 1.2 (t, 3H), 1.4 (m, 2H), 1.6–1.8 (m, 10H), 2.3 (m, 2H), 2.9 (m, 4H), 6.6 (m, 2H), 7.8 (m, 2H), 11.7 (s, 1H) ppm.

Example 9 cis-Ethyl (2E)-3-{3-[7-(4-tert-butylcyclohexyl)-5-ethyl-4-oxo-3,4-dihydroimidazo-[5,1-f][1,2,4]triazin-2-yl]phenyl}-2-propenoate

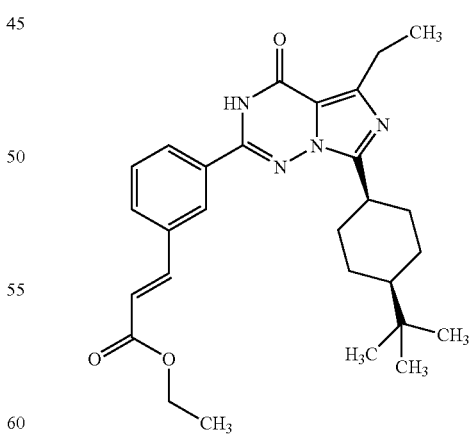

740 mg (1.62 mmol) cis-2-(3-bromophenyl)-7-(4-tert-butylcyclohexyl)-5-ethylimidazo[5,1-f][1,2,4]triazin-4 (3H)-one (Example 27A), 1.6 g (16.2 mmol) ethyl acrylate, 327 mg (3.24 mmol) triethylamine and 227 mg (0.32 mmol) dichlorobis(triphenylphosphine)palladium(II) are stirred at 120° C. in 20 ml DMF in an argon atmosphere for 18 hours.

After cooling down to room temperature, the mixture is filtrated over Celite, and the product is isolated by column chromatography or preparative HPLC.

Yield: 447 mg (58%)

$^1$H-NMR (DMSO-d$_6$, 200 MHz): δ=0.8 (s, 9H), 1.1 (m, 1H), 1.2 (t, 3H), 1.3 (t, 3H), 1.5–1.7 (m, 6H), 2.2 (m, 2H), 2.9 (q, 2H), 3.6 (m, 1H), 4.2 (q, 2H), 6.8 (d, 1H), 7.6 (m, 1H), 7.7 (d, 1H), 7.9 (m, 1H), 8.0 (m, 1H), 8.4 (m, 1H), 11.8 (s, 1H) ppm.

Example 10 cis-(2E)-3-{3-[7-(4-tert-Butylcyclohexyl)-5-ethyl-4-oxo-3,4-dihydroimidazo[5,1-f]-[1,2,4]triazin-2-yl]phenyl}-2-propenoic acid

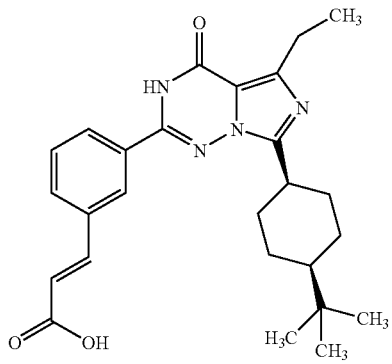

200 mg (0.42 mmol) of Example 9 are dissolved in 5 ml ethanol, 5 ml sodium hydroxide (10% in water) are added and the mixture is stirred at room temperature for 18 hours. Hydrochloric acid is added (pH<7), followed by dichloromethane. The phases are separated, the organic phase is dried over sodium sulfate and evaporated to dryness in vacuo. The product is purified by column chromatography or preparative HPLC.

Yield: 177 mg (94%)

$^1$H-NMR (DMSO-d$_6$, 300 MHz): δ=0.8 (s, 9H), 1.1 (m, 1H), 1.2 (t, 3H), 1.5–1.7 (m, 6H), 2.2 (m, 2H), 2.9 (q, 2H), 3.6 (m, 1H), 6.7 (d, 1H), 7.6 (m, 2H), 7.8 (m, 1H), 8.0 (m, 1H), 8.3 (m, 1H) ppm.

Example 11 cis-(2E)-3-{3-[7-(4-tert-Butylcyclohexyl)-5-ethyl-4-oxo-3,4-dihydroimidazo[5,1-f]-[1,2,4]triazin-2-yl]phenyl}-N-propyl-2-propenamide

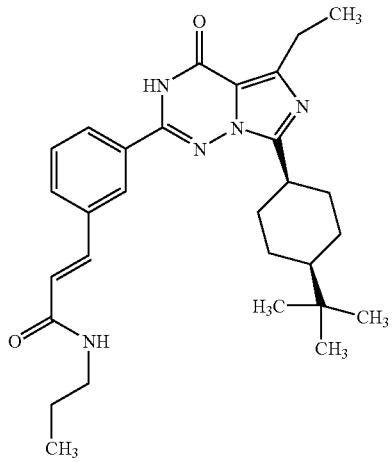

In analogy to the procedure for Example 3, 70 mg (0.16 mmol) of Example 10, 18 mg (0.31 mmol) n-propylamine and proportionate amounts of the other reagents are used.

Yield: 59 mg (70%)

$^1$H-NMR (DMSO-d$_6$, 300 MHz): δ=0.8 (s, 9H), 0.9 (t, 3H), 1.1 (m, 1H), 1.2 (t, 3H), 1.5 (m, 2H), 1.5–1.7 (m, 6H), 2.2 (m, 2H), 2.9 (q, 2H), 3.2 (q, 2H), 3.7 (d, 1H), 6.7 (d, 1H), 7.5 (d, 1H), 7.6 (m, 1H), 7.9 (m, 1H), 8.2 (m, 1H), 8.3 (m, 1H), 11.9 (m, 1H) ppm.

Example 12 cis-(2E)-3-{3-[7-(4-tert-Butylcyclohexyl)-5-ethyl-4-oxo-3,4-dihydroimidazo[5,1-f]-[1,2,4]triazin-2-yl]phenyl}-N,N-diethyl-2-propenamide

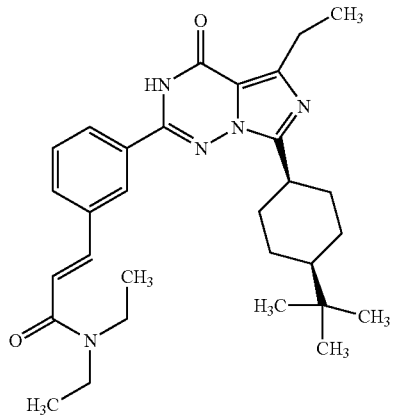

In analogy to the procedure for Example 3, 65 mg (0.14 mmol) of Example 10, 21 mg (0.29 mmol) diethylamine and proportionate amounts of the other reagents are used.

Yield: 31 mg (43%)

$^1$H-NMR (DMSO-d$_6$, 300 MHz): δ=0.8 (s, 9H), 1.1 (br. t, 3H; m, 1H), 1.2 (br. t, 3H; t, 3H), 1.5–1.7 (m, 6H), 2.2 (m, 2H), 2.9 (q, 2H), 3.4 (m, 2H), 3.6 (m, 3H), 7.2 (d, 1H), 7.5 (d, 1H), 7.6 (m, 1H), 7.9 (m, 2H), 8.2 (m, 1H), 11.8 (s, 1H) ppm.

Example 13 cis-Ethyl 3-{3-[7-(4-tert-butylcyclohexyl)-5-ethyl-4-oxo-3,4-dihydroimidazo[5,1-f]-[1,2,4]triazin-2-yl]phenyl}propanoate

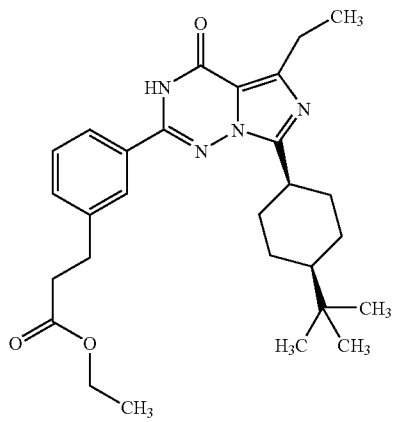

In analogy to the procedure for Example 6, 178 mg (0.37 mmol) of Example 9 are dissolved in 10 ml methanol and hydrogenated. The product is purified by column chromatography.

Yield: 147 mg (82%)

$^1$H-NMR (DMSO-$d_6$, 300 MHz): δ=0.8 (s, 9H), 1.1 (m, 1H), 1.2 (t, 3H), 1.3 (t, 3H), 1.5–1.7 (m, 6H), 2.2 (m, 2H), 2.7 (t, 2H), 2.9 (m, 4H), 3.6 (m, 1H), 4.1 (q, 2H), 7.4 (m, 2H), 7.7 (m, 1H), 7.8 (m, 1H), 11.7 (s, 1H) ppm.

Example 14 cis-3-{3-[7-(4-tert-Butylcyclohexyl)-5-ethyl-4-oxo-3,4-dihydroimidazo[5,1-f][1,2,4]-triazin-2-yl]phenyl}propanoic acid

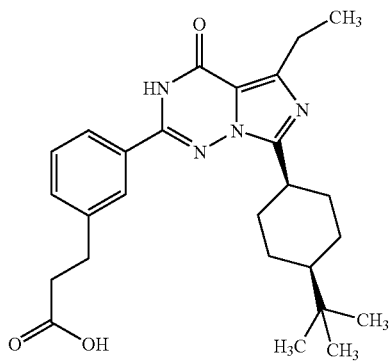

In analogy to the procedure for Example 10, 170 mg (0.36 mmol) of Example 13 are used.

Yield: 70 mg (44%)

$^1$H-NMR (DMSO-$d_6$, 300 MHz): δ=0.8 (s, 9H), 1.1 (m, 1H), 1.2 (t, 3H), 1.5–1.7 (m, 6H), 2.2 (m, 2H), 2.6 (t, 2H), 2.9 (m, 4H), 3.6 (m, 1H), 7.4 (m, 2H), 7.8 (m, 1H), 7.9 (m, 1H) ppm.

Example 15 cis-4-[7-(4-tert-Butylcyclohexyl)-5-ethyl-4-oxo-3,4-dihydroimidazo[5,1-f][1,2,4]-triazin-2-yl]benzoic acid

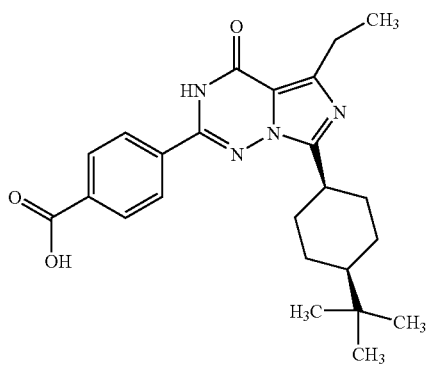

500 mg (1.24 mmol) of Example 23A are dissolved in 25 ml ethanol and 25 ml concentrated hydrochloric acid. The mixture is stirred at 110° C. for 18 hours. After cooling down to room temperature, an aqueous solution of sodium hydroxide is added to achieve a pH of 6–7. Ethyl acetate is then added, the organic phase dried over sodium sulfate and evaporated to dryness in vacuo. The product is purified by chromatography (flash or column chromatography or preparative HPLC).

Yield: 327 mg $^1$H-NMR (DMSO-$d_6$, 300 MHz): δ=0.8 (s, 9H), 1.1 (m, 1H), 1.2 (t, 3H), 1.5–1.7 (m, 6H), 2.2 (m, 2H), 2.9 (t, 2H), 3.6 (m, 1H), 8.0 (m, 4H) ppm.

Example 16 cis-4-[7-(4-tert-Butylcyclohexyl)-5-ethyl-4-oxo-3,4-dihydroimidazo[5,1-f][1,2,4]-triazin-2-yl]benzamide

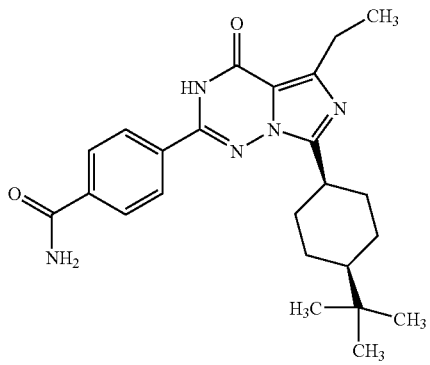

Using the procedure for the preparation of Example 15, Example 16 was obtained as a by-product.

Yield: 75 mg (16%)

LC/MS (A): MS (ESI): 422 (M+H)$^+$, retention time 2.69 min.

Example 17 cis-4-[7-(4-tert-Butylcyclohexyl)-5-ethyl-4-oxo-3,4-dihydroimidazo[5,1-f][1,2,4]-triazin-2-yl]-N-propyl-benzamide

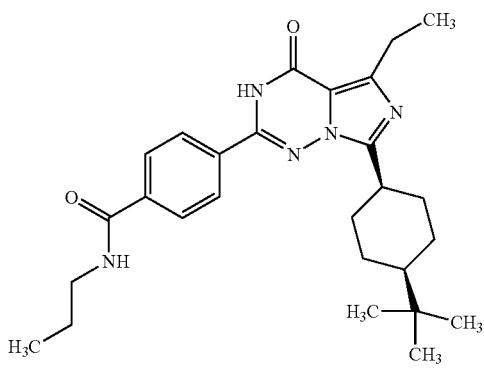

In analogy to the procedure for Example 3, 35 mg (0.08 mmol) of Example 15, 5 mg (0.09 mmol) n-propylamine and proportionate amounts of the other reagents are used.

Yield: 27 mg (71%)

¹H-NMR (DMSO-d₆, 300 MHz): δ=0.8 (s, 9H), 0.9 (t, 3H), 1.1 (m, 1H), 1.2 (t, 3H), 1.5–1.7 (m, 8H), 2.2 (m, 1H), 2.9 (q, 2H), 3.3 (m, 2H), 3.6 (m, 1H), 8.0 (m, 4H), 8.6 (br. t, 1H), 11.9 (s, 1H) ppm.

Example 18 cis-4-[7-(4-tert-Butylcyclohexyl)-5-ethyl-4-oxo-3,4-dihydroimidazo[5,1-f][1,2,4]-triazin-2-yl]-N,N-diethylbenzamide

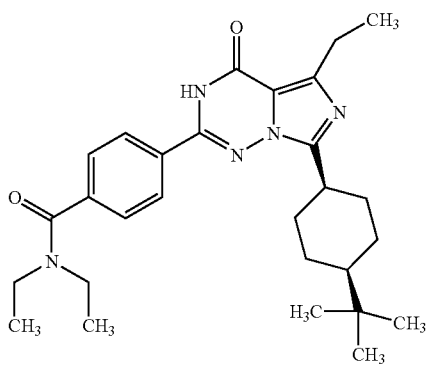

In analogy to the procedure for Example 3, 32 mg (0.08 mmol) of Example 15, 6 mg (0.08 mmol) diethylamine and proportionate amounts of the other reagents are used.

Yield: 31 mg (85%)

¹H-NMR (DMSO-d₆, 300 MHz): δ=0.8 (s, 9H), 1.1 (m, 7H), 1.2 (t, 3H), 1.5–1.7 (m, 8H), 2.2 (m, 1H), 2.9 (q, 2H), 3.2 (br. m, 2H), 3.4 (br. m, 2H), 3.6 (m, 1H), 7.5 (m, 2H), 8.0 (m, 2H), 11.8 (s, 1H) ppm.

Example 19 cis-4-[7-(4-tert-Butylcyclohexyl)-5-ethyl-4-oxo-3,4-dihydroimidazo[5,1-f][1,2,4]-triazin-2-yl]-N-cyclohexylbenzamide

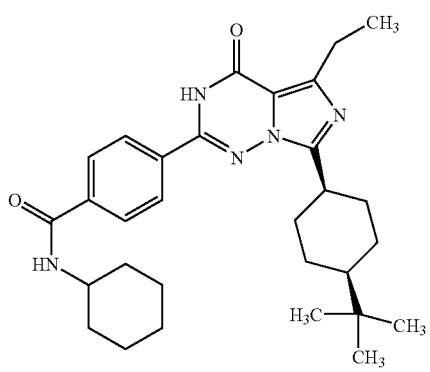

In analogy to the procedure for Example 3, 32 mg (0.08 mmol) of Example 15, 8 mg (0.08 mmol) cyclohexylamine and proportionate amounts of the other reagents are used.

Yield: 31 mg (80%)

¹H-NMR (DMSO-d₆, 300 MHz): δ=0.8 (s, 9H), 1.1 (m, 1H), 1.2 (t, 3H), 1.3 (m, 4H), 1.5–1.8 (m, 10H), 1.9 (m, 2H), 2.2 (m, 2H), 2.9 (q, 21), 3.6 (m, 1H), 3.8 (m, 1H), 7.9 (m, 2H), 8.0 (m, 2H), 8.3 (d, 1H), 11.9 (s, 1H) ppm.

Example 20 cis-4-[7-(4-tert-Butylcyclohexyl)-5-ethyl-4-oxo-3,4-dihydroimidazo[5,1-f][1,2,4]-triazin-2-yl]-N-cyclohexyl-N-methylbenzamide

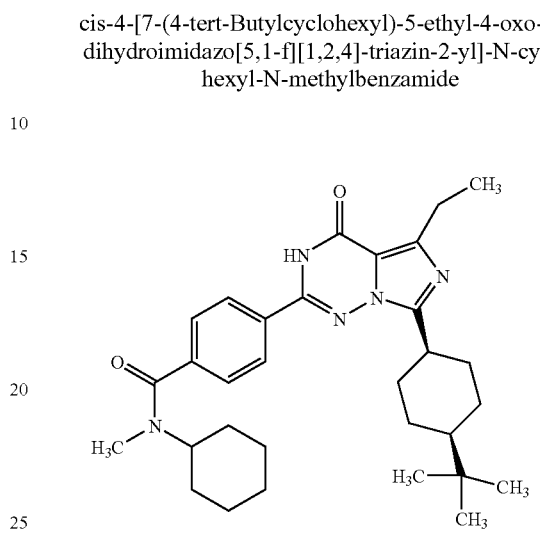

In analogy to the procedure for Example 3, 32 mg (0.08 mmol) of Example 15, 9 mg (0.08 mmol) N-methylcyclohexylamine and proportionate amounts of the other reagents are used.

Yield: 35 mg (88%)

¹H-NMR (DMSO-d₆, 300 MHz): δ=0.8 (s, 9H), 1.1 (m, 1H), 1.2 (t, 3H), 1.5–1.8 (m, 16H), 2.2 (m, 2H), 2.8 (m, 1H), 2.9 (q, 2H), 3.6 (m, 1H), 7.5 (m, 2H), 8.0 (m, 2H) ppm.

Example 21 cis-7-(4-tert-Butylcyclohexyl)-5-ethyl-2-[4-(4-morpholinylcarbonyl)phenyl]imidazo-[5,1-f][1,2,4]triazin-4(3H)-one

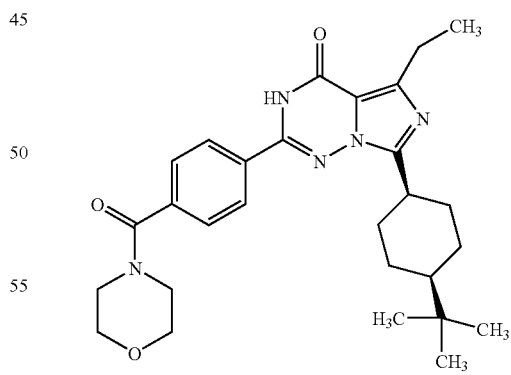

In analogy to the procedure for Example 3, 32 mg (0.08 mmol) of Example 15, 7 mg (0.08 mmol) morpholine and proportionate amounts of the other reagents are used.

Yield: 31 mg (82%)

¹H-NMR (DMSO-d₆, 300 MHz): δ=0.8 (s, 9H), 1.1 (m, 1H), 1.2 (t, 3H), 1.5–1.8 (m, 6H), 21.2 (m, 2H), 2.9 (q, 2H), 3.6 (m, 9H), 7.5 (m, 2H), 8.0 (m, 2H), 11.9 (s, 1H) ppm.

Example 22 cis-7-(4-tert-Butylcyclohexyl)-5-ethyl-2-[4-(1-piperidinylcarbonyl)phenyl]imidazo-[5,1-f][1,2,4]triazin-4(3H)-one

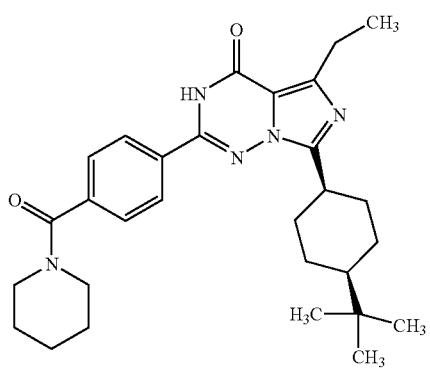

In analogy to the procedure for Example 3, 32 mg (0.08 mmol) of Example 15, 7 mg (0.08 mmol) piperidine and proportionate amounts of the other reagents are used.

Yield: 31 mg (83%)

$^1$H-NMR (DMSO-$d_6$, 300 MHz): δ=0.8 (s, 9H), 1.1 (m, 1H), 1.2 (t, 3H), 1.5–1.7 (m, 14H), 2.2 (m, 2H), 2.9 (q, 2H), 3.6 (m, 3H), 7.5 (m, 2H), 8.0 (m, 2H), 11.9 (s, 1H) ppm.

Example 23 cis-3-[7-(4-tert-Butylcyclohexyl)-5-ethyl-4-oxo-3,4-dihydroimidazo[5,1-f][1,2,4]-triazin-2-yl]benzamide

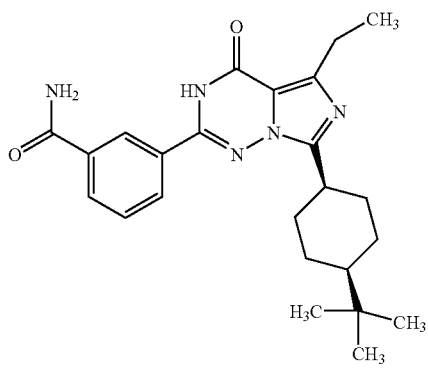

100 mg (0.25 mmol) cis-3-[7-(4-tert-butylcyclohexyl)-5-ethyl-4-oxo-3,4-dihydroimidazo[5,1-f][1,2,4]triazin-2-yl]benzonitrile (Example 40A) are dissolved in 5 ml ethanol and 10 ml water. 342 mg (2.48 mmol) potassium carbonate and 281 mg (2.48 mmol) hydrogene peroxide are added. The reaction mixture is stirred at room temperature for 18 hours. Dichloromethane is added, the organic phase separated, dried over sodium sulfate and evaporated to dryness in vacuo.

Yield: 97.6 mg (93%)

$^1$H-NMR (DMSO-$d_6$, 300 MHz): δ=0.8 (s, 9H), 1.1 (m, 1H), 1.2 (t, 3H), 1.5–1.7 (m, 6H), 2.2 (m, 2H), 2.9 (q, 2H), 3.6 (m, 1H), 7.5 (m, 1H), 7.6 (m, 1H), 8.1 (m, 3H), 8.4 (m, 1H), 11.8 (s, 1H) ppm.

Example 24 cis-3-[7-(4-tert-Butylcyclohexyl)-5-ethyl-4-oxo-3,4-dihydroimidazo[5,1-f][1,2,4]-triazin-2-yl]benzoic acid

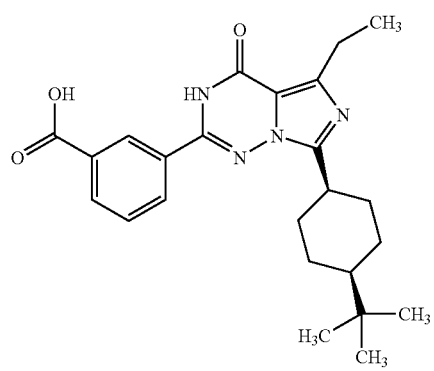

108 mg (0.27 mmol) cis-3-[7-(4-tert-butylcyclohexyl)-5-ethyl-4-oxo-3,4-dihydroimidazo[5,1-f][1,2,4]triazin-2-yl]benzonitrile (Example 40A) are dissolved in concentrated hydrochloric acid, and the reaction mixture is stirred at 95° C. for three hours. Sodium hydroxide (10% aqueous solution) (until a pH of 6–7 is achieved) and ethylacetate are added. The organic phase is dried over sodium sulfate and evaporated to dryness in vacuo. The product is purified by column chromatography.

Yield: 15 mg (13%)

$^1$H-NMR (DMSO-$d_6$, 300 MHz): δ=0.8 (s, 9H), 1.1 (m, 1H), 1.2 (t, 3H), 1.5–1.7 (m, 6H), 2.2 (m, 2H), 2.9 (q, 2H), 3.6 (m, 1H), 7.5 (m, 1H), 8.0 (m, 1H), 8.1 (8m, 1H), 8.5 (m, 1H) ppm.

Example 25 cis-Ethyl (2E)-3-{4-[7-(4-tert-butylcyclohexyl)-5-ethyl-oxo-3,4-dihydroimidazo-[5,1-f][1,2,4]triazin-2-yl]phenyl}-2-propenoate

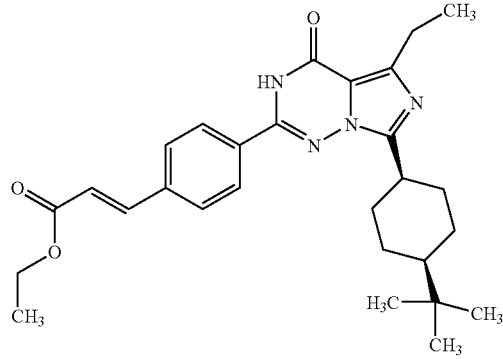

In analogy to the procedure for Example 9, 3.0 g (6.56 mmol) of Example 30A, 6.57 g (65.69 mmol) ethyl acrylate and proportionate amounts of the other reagents are used.

Yield: 1.81 g (58%)

$^1$H-NMR (DMSO-$d_6$, 300 MHz): δ=0.8 (s, 9H), 1.1 (m, 1H), 1.2 (t, 3H), 1.3 (t, 3H), 1.5–1.7 (m, 6H), 2.2 (m, 2H), 2.9 (q, 2H), 3.6 (m, 1H), 4.2 (q, 2H), 6.8 (d, 1H), 7.7 (d, 1H), 7.9 (m, 2H), 8.0 (m, 2H), 11.8 (s, 1H) ppm.

Example 26 cis-(2E)-3-{4-[7-(4-tert-Butylcyclohexyl)-5-ethyl-4-oxo-3,4-dihydroimidazo[5,1-f]-[1,2,4]triazin-2-yl]phenyl}-2-propenoic acid

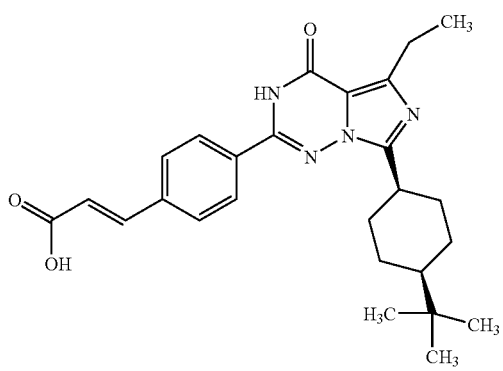

In analogy to the procedure for Example 10, 882 mg (1.85 mmol) of Example 25 are used.

Yield: 529 g (64%)

$^1$H-NMR (DMSO-$d_6$, 200 MHz): δ=0.8 (s, 9H), 1.1 (m, 1H), 1.2 (t, 3H), 1.5–1.7 (m, 6H), 2.2 (m, 2H), 2.9 (q, 2H), 3.6 (m, 1H), 6.7 (d, 1H), 7.7 (d, 1H), 7.9 (m, 2H), 8.0 (m, 2H), 12.1 (s, 1H) ppm.

Example 27 cis-Ethyl 3-{4-[7-(4-tert-butylcyclohexyl)-5-ethyl-4-oxo-3,4-dihydroimidazo[5,1-f]-[1,2,4]triazin-2-yl]phenyl}propanoate

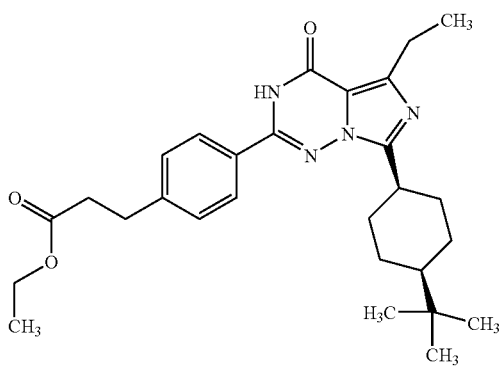

In analogy to the procedure for Example 6, 900 mg (1.89 mmol) of Example 25 are dissolved in 10 ml methanol and hydrogenated. The product is purified by column chromatography.

Yield: 368 mg (41%)

$^1$H-NMR (DMSO-$d_6$, 300 MHz): δ=0.8 (s, 9H), 1.1 (m, 1H), 1.2 (t, 3H), 1.3 (t, 3H), 1.5–1.7 (m, 6H), 2.2 (m, 2H), 2.7 (t, 2H), 2.9 (m, 4H), 3.6 (m, 1H), 4.1 (q, 2H), 7.4 (m, 2H), 7.9 (m, 1H), 11.7 (s, 1H) ppm.

Example 28 cis-3-{4-[7-(4-tert-Butylcyclohexyl)-5-ethyl-4-oxo-3,4-dihydroimidazo[5,1-f][1,2,4]-triazin-2-yl]phenyl}propanoic acid

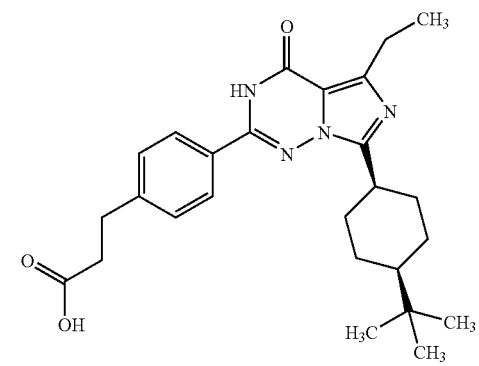

In analogy to the procedure for Example 10, 368 mg (0.77 mmol) of Example 27 are used.

Yield: 269 mg (78%)

$^1$H-NMR (DMSO-$d_6$, 300 MHz): δ=0.8 (s, 9H), 1.1 (m, 1H), 1.2 (t, 3H), 1.5–1.7 (m, 6H), 2.2 (m, 2H), 2.6 (t, 2H), 2.9 (m, 4H), 3.6 (m, 1H), 7.4 (m, 2H), 7.8 (m, 1H), 7.9 (m, 1H), 12.0 (br, 2H) ppm.

Example 29

2-(3-Aminophenyl)-7-cyclopentyl-5-ethylimidazo[5,1-f][1,2,4]triazin-4(3H)-one

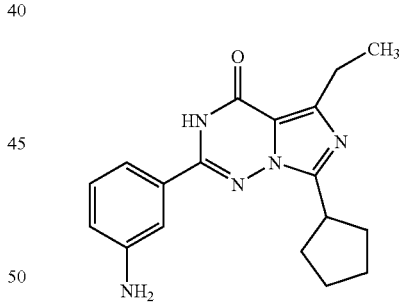

1.8 g (5.1 mmol) 7-cyclopentyl-5-ethyl-2-(3-nitrophenyl)imidazo[5,1-f][1,2,4]triazin-4(3H)-one (Example 21A) are dissolved in 100 ml methanol, and 200 mg palladium (10% on charcoal) are added. The mixture is exposed to an hydrogen atmosphere until no more hydrogen is absorbed. Then the palladium/charcoal is removed by filtration and the filtrate is evaporated to dryness in vacuo. The product is purified by chromatography (flash or column chromatography).

Yield: 1.1 g (67%)

$^1$H-NMR (400 MHz, CD$_3$OD): δ=1.27 (t, 3H), 1.60–2.18 (m, 8H), 3.01 (q, 2H), 3.63–3.74 (m, 1H), 7.79 (d, 1H), 7.14 (t, 1H), 7.48–7.56 (m, 2H) ppm.

Example 30 cis-2-(3-Aminophenyl)-7-(4-tert-butylcyclohexyl)-5-ethylimidazo[5,1-f][1,2,4]-triazin-4(3H)-one

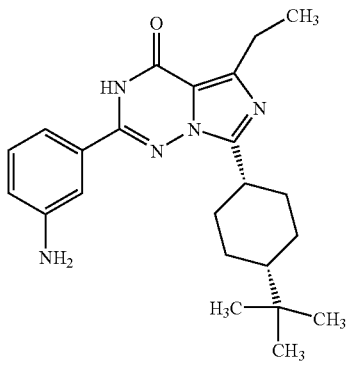

In analogy to the procedure for Example 29, 3.0 g (71 mmol) cis-7-(4-tert-butylcyclohexyl)-5-ethyl-2-(3-nitrophenyl)imidazo[5,1-f][1,2,4]triazin-4(3H)-one (Example 22A) and proportionate amounts of the other reagents are used.

Yield: 300 mg (11%)

$^1$H-NMR (300 MHz, DMSO-$d_6$): δ=0.83 (s, 9H), 1.03–1.16 (m, 1H), 1.23 (t, 3H), 1.49–1.75 (m, 6H), 2.14–2.23 (m, 2H), 2.89 (q, 2H), 3.50–3.56 (m, 1H), 5.30–5.36 (m, 1H), 7.75 (d, 1H), 7.05 (d, 1H), 7.09–7.19 (m, 2H) ppm.

Example 31

N-[3-(7-Cyclopentyl-5-ethyl-4-oxo-3,4-dihydroimidazo[5,1-f][1,2,4]triazin-2-yl)phenyl]-2,2-dimethylpropanamide

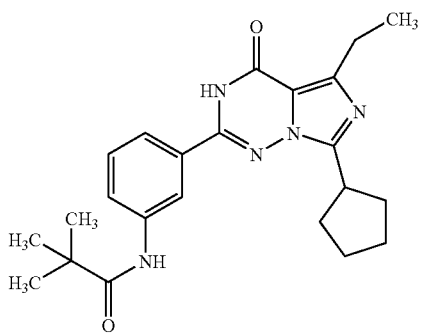

50 mg (0.16 mmol) 2-(3-aminophenyl)-7-cyclopentyl-5-ethylimidazo[5,1-f][1,2,4]-triazin-4(3H)-one (Example 29) and 78 mg (0.77 mmol) triethylamine are dissolved in 4 ml dichloromethane. 37 mg (0.31 mmol) 2,2-dimethylpropanoyl chloride are added dropwise. The mixture is stirred for 2 hours at room temperature and then washed with 1 N potassium hydrogensulfate solution and with saturated sodium hydrogencarbonate solution. The organic layers are dried and evaporated to dryness in vacuo. The product is purified by chromatography (flash or column chromatography).

Yield: 11 mg (17%)

$^1$H-NMR (400 MHz, CD$_3$OD): δ=1.28 (t, 3H), 1.32 (s, 9H), 1.67–2.20 (m, 8H), 2.97 (q, 2H), 3.72 (m, 1H), 7.49 (t, 1H), 7.66 (d, 1H), 7.74 (d, 1H), 8.15 (s, 1H) ppm.

Example 32

N-Benzoyl-N-[3-(7-cyclopentyl-5-ethyl-4-oxo-3,4-dihydroimidazo[5,1-f][1,2,4]triazin-2-yl)phenyl]benzamide

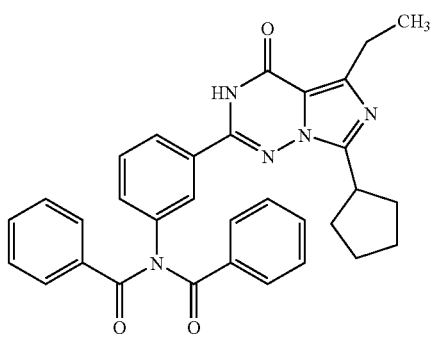

In analogy to the procedure for Example 31, 50 mg (0.15 mmol) 2-(3-aminophenyl)-7-cyclopentyl-5-ethylimidazo[5,1-f][1,2,4]triazin-4(3H)-one (Example 29), 43 mg (0.31 mmol) benzoyl chloride and proportionate amounts of the other reagents are used.

Yield: 20 mg (19%)

$^1$H-NMR (400 MHz, CDCl$_3$): δ=1.31 (t, 3H), 1.62–2.20 (m, 8H), 3.00 (q, 2H), 3.64 (quin., 1H), 7.18 (d, 1H), 7.35–7.97 (m, 12H), 8.09 (d, 1H) ppm.

Example 33 cis-N-{3-[7-(4-tert-Butylcyclohexyl)-5-ethyl-4-oxo-3,4-dihydroimidazo[5,1-][1,2,4]-triazin-2-yl]phenyl}acetamide

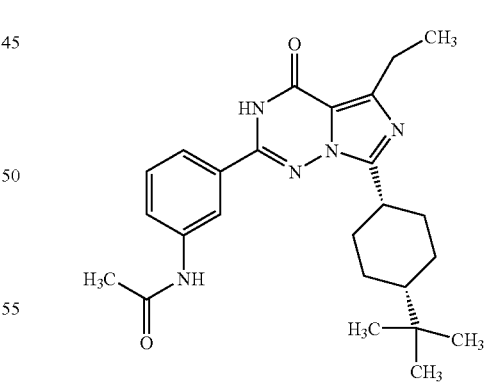

5.0 mg (0.076 mmol) acetic acid, 10 mg (0.076 mmol) 1-hydroxy-1H-benzotriazole hydrate and 19 mg (0.19 mmol) 4-methylmorpholine are dissolved in dichloromethane. The reaction mixture is cooled down to −10° C., then 15 mg (0.076 mmol) 1-(3-dimethylaminopropyl)-3-ethylcarbodiimide hydrochloride are added. The mixture is stirred for 30 min while warming up nearly to room temperature, then it is cooled down again to −10° C. After addition of 25 mg (0.064 mmol) cis-2-(3-aminophenyl)-7-(4-tert-butylcyclohexyl)-5-ethylimidazo[5,1-f][1,2,4]triazin-4(3H)-one (Example 30) the mixture is stirred for 2 hours without further cooling. Then it is washed with 1 N potassium hydrogensulfate solution and with saturated sodium hydrogencarbonate solution. The organic layers are dried and evaporated to dryness in vacuo. The product is purified by chromatography (flash or column chromatography).

Yield: 20 mg (72%)

$^1$H-NMR (400 MHz, CD$_3$OD): δ=0.86 (s, 9H), 1.09–1.20 (m, 1H), 1.29 (t, 3H), 1.49–1.68 (m, 4H), 1.71–1.82 (m, 2H), 2.16 (s, 3H), 2.36–2.45 (m, 2H), 2.99 (q, 2H), 3.55–3.60 (m, 1H), 7.48 (t, 1H), 7.63 (d, 1H), 7.74 (d, 1H), 8.16 (s, 1H) ppm.

Example 34

2-[3-(Benzylamino)phenyl]-7-cyclopentyl-5-ethylimidazo[5,1-f][1,2,4]triazin-4(3H)-one

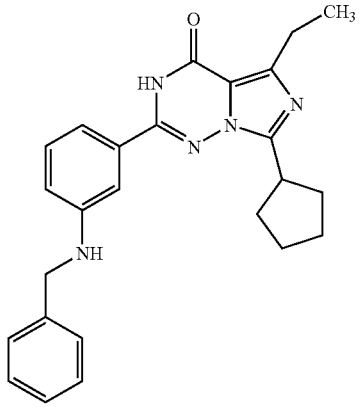

In analogy to the procedure for Example 8, 100 mg (0.31 mmol) 2-(3-aminophenyl)-7-cyclopentyl-5-ethylimidazo[5,1-f][1,2,4]triazin-4(3H)-one (Example 29), 52 mg (0.49 mmol) benzaldehyde and proportionate amounts of the other reagents are used.

Yield: 14 mg (10%)

$^1$H-NMR (400 MHz, CD$_3$OD): δ=1.28 (t, 3H), 1.69–2.17 (m, 8H), 2.96 (q, 2H), 3.62 (quin., 1H), 4.39 (s, 2H), 6.82 (d, 1H), 7.10 (d, 1H), 7.17 (s, 1H), 7.18–7.25 (m, 2H), 7.27–7.33 (m, 2H), 7.35–7.41 (m, 2H) ppm.

Example 35

4-(7-Cyclopentyl-5-ethyl-4-oxo-3,4-dihydroimidazo[5,1-f][1,2,4]triazin-2-yl)benzamide

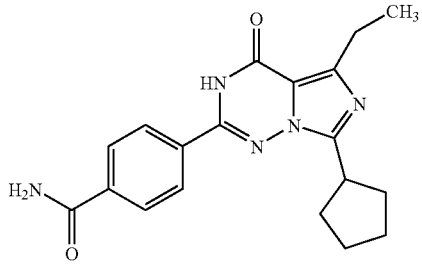

45 mg (0.12 mmol) of Example 11A are suspended in 10 ml dichloroethane, and 165 mg (1.07 mmol) phosphoroxychloride are added. The mixture is evaporated to dryness in vacuo. The product is purified by preparative HPLC.

Yield: 4 mg (9%)

LC/MS (A): MS (ESI): 351 (M+H)$^+$, retention time 2.84 min.

We claim:

1. A compound of the general formula (I)

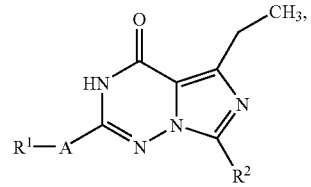

in which

A denotes phenylene or pyridinylene, which can be substituted by 0 to 3 residues selected independently from the group consisting of halogen, (C$_1$–C$_4$)-alkyl, trifluoromethyl, cyano, nitro, (C$_1$–C$_4$)-alkoxy and trifluoromethoxy, R$^1$ denotes hydroxy or a group of the formula —NR$^3$R$^4$, —X—C(=O)—OR$^5$ or —X—C(=O)—NR$^6$R$^7$, wherein X denotes a bond, —CH$_2$—, —CH$_2$—CH$_2$— or —CH=CH—, R$^3$ and R$^4$ are independently selected from the group consisting of hydrogen, (C$_1$–C$_6$)-alkyl, (C$_3$–C$_7$)-cycloalkyl, (C$_1$–C$_6$)-alkanoyl and (C$_6$–C$_{10}$)-aroyl, wherein (C$_1$–C$_6$)-alkyl can be further substituted with 0 to 3 substituents selected independently from the group consisting of (C$_3$–C$_7$)-cycloalkyl and (C$_6$–C$_{10}$)-aryl, R$^5$ denotes hydrogen or (C$_1$–C$_6$)-alkyl, R$^6$ and R$^7$ are independently selected from the group consisting of hydrogen, (C$_1$–C$_6$)-alkyl, (C$_3$–C$_7$)-cycloalkyl and (C$_6$–C$_{10}$)-aryl, or together with the nitrogen atom to which they are attached form a 4- to 7-membered heterocyclic ring which may contain one additional ring heteroatom selected from N, O or S, R$^2$ denotes (C$_3$–C$_{10}$)-cycloalkyl, which is optionally substituted up to two times by residues selected independently from the group consisting of (C$_1$–C$_6$)-alkyl, (C$_1$–C$_6$)-alkoxy, hydroxy, halogen, trifluoromethyl and oxo.

2. A compound according to claim 1, whereby

A denotes 1,3- or 1,4-phenylene, which can be substituted by 0 to 3 residues selected independently from the group consisting of fluoro, chloro, bromo, methyl, trifluoromethyl methoxy, ethoxy and trifluoromethoxy, R$^1$ denotes hydroxy or a group of the formula —NR$^3$R$^4$, —X—C(=O)—OR$^5$ or —X—C(=O)—NR$^6$R$^7$, wherein X denotes a bond, —CH$_2$—CH$_2$— or —CH=CH—, R$^3$ denotes hydrogen, R$^4$ denotes hydrogen, (C$_1$–C$_4$)-alkyl or (C$_1$–C$_5$)-alkanoyl, wherein (C$_1$–C$_4$)-alkyl can be further substituted with 0 to 3 substituents selected independently from the group consisting of cyclopentyl, cyclohexyl or phenyl, R$^5$ denotes hydrogen, R$^6$ and R$^7$ are independently selected from the group consisting of hydrogen, (C$_1$–C$_4$)-alkyl and (C$_5$–C$_6$)-cycloalkyl, or together with the nitrogen atom to which they are attached form a 5- to 6-membered heterocyclic ring which may contain one additional ring heteroatom selected from N, O or S, $R^2$ denotes $(C_4-C_7)$-cycloalkyl, which is optionally substituted up to two times by residues independently selected from the group consisting of $(C_1-C_4)$-alkyl, $(C_1-C_4)$-alkoxy, hydroxy, fluoro, trifluoromethyl and oxo.

3. A compound according to claim 1 or 2, whereby

A denotes 1,3- or 1,4-phenylene, $R^1$ denotes hydroxy or a group of the formula $-NR^3R^4$, $-X-C(=O)-OR^5$ or $-X-C(=O)-NR^6R^7$, wherein X denotes a bond, $R^3$ denotes hydrogen, $R^4$ denotes hydrogen, $(C_1-C_4)$-alkyl, $(C_1-C_5)$-alkanoyl, cyclohexylmethyl or benzyl, $R^5$ denotes hydrogen, $R^6$ denotes hydrogen, methyl or ethyl, $R^7$ denotes hydrogen, $(C_1-C_4)$-alkyl, cyclopentyl or cyclohexyl, or $R^6$ and $R^7$ together with the nitrogen atom to which they are attached form a morpholino or piperidino ring, $R^2$ denotes $(C_4-C_6)$-cycloalkyl, which is optionally substituted up to two times by identical or different $(C_1-C_4)$-alkyl residues.

4. A compound according to claim 1 or 2, whereby

A denotes 1.3- or 1,4-phenylene, $R^1$ denotes hydroxy or a group of the formula $-NR^3R^4$, $-X-C(=O)-OR^5$ or $-X-C(=O)-NR^6R^7$, wherein X denotes a bond, $R^3$ denotes hydrogen, $R^4$ denotes hydrogen, $(C_1-C_4)$-alkyl, $(C_1-C_5)$-alkanoyl, cyclohexyl methyl or benzyl, $R^5$ denotes hydrogen, $R^6$ denotes hydrogen, methyl or ethyl, $R^7$ denotes hydrogen, $(C_1-C_4)$-alkyl, cyclopentyl or cyclohexyl, or $R^6$ and $R^7$ together with the nitrogen atom to which they are attached form a morpholino or piperidino ring.

5. A process for the preparation of a compound according to claim 1, characterized in that a compound of the general formula (IV)

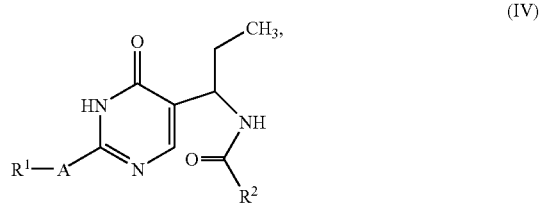

in which

A, $R^1$ and $R^2$ are defined as in claim 1, is reacted with a dehydrating agent.

6. Pharmaceutical composition containing one or more compounds according to claim 1 and a pharmacologically acceptable diluent.

7. A method for the prevention and treatment of a chronic inflammatory lung disease, comprising administering to a patient in need thereof a therapeutically effective amount of a compound of claim 1.

8. The method of claim 7, wherein the chronic inflammatory lung disease is chronic obstructive pulmonary disease or asthma.

* * * * *